United States Patent [19]

Chamoun

[11] Patent Number: 5,020,540
[45] Date of Patent: Jun. 4, 1991

[54] CARDIAC BIOPOTENTIAL ANALYSIS SYSTEM AND METHOD

[75] Inventor: Nassib G. Chamoun, Dedham, Mass.
[73] Assignee: Biometrak Corporation, Cambridge, Mass.
[21] Appl. No.: 396,990
[22] Filed: Aug. 22, 1989

Related U.S. Application Data

[63] Continuation-in-part of Ser. No. 107,419, Oct. 9, 1987.
[51] Int. Cl.$^5$ ............................................... A61B 5/04
[52] U.S. Cl. .................................. 128/696; 128/702; 128/703; 364/413.06
[58] Field of Search ................... 128/696, , 697, 702, 128/703, 708; 364/413.05, 413.06

[56] References Cited

U.S. PATENT DOCUMENTS

| | | | |
|---|---|---|---|
| 3,995,622 | 12/1976 | Nordgren et al. | 128/703 |
| 4,680,708 | 7/1987 | Ambos et al. | 128/703 |
| 4,732,158 | 3/1988 | Sadeh | 128/702 |
| 4,742,458 | 5/1988 | Nathans et al. | 128/702 |

OTHER PUBLICATIONS

J. N. Hershleb, Signal Analysis of Ventricular Fibrillation.
N. G. Chamoun, Bispectral Analysis of Phase Locking in the R-R Interval Series.
N. G. Chamoun, Autonomic Control of Phase Locking in the R-R Interval Series as Assessed by the Bispectrum.
N. G. Chamoun, Bispectral Properties of the R-R Interval Time Series.
Brillinger, D. R. An Introduction to Polyspectra.
Huber, P. J., Statistical Method for Investigating Phase Relations in Stationary Stochastic Processes.
Tyron, P. V., The Bispectrum and Higher-Order Spectra: A Bibliography.
Nikias, C. L., Bispectrum Estimation: A Digital Signal Processing Framework.
Kleiner, N., Analysis of the Interelations Between Frequency Bands of the EEG by Means of the Bispectrum.
Dumermuth, G., Analysis of the Interrelations Between Frequency Bands of the EEG by Means of the Bispectrum.

(List continued on next page.)

Primary Examiner—Francis J. Jaworski
Assistant Examiner—George Manuel
Attorney, Agent, or Firm—Hale and Dorr

[57] ABSTRACT

Disclosed is a cardiac biopotential analysis system and method for detecting and quantifying in a noninvasive manner nonlinear dynamic patterns of depolarization and repolarization on a beat to beat basis in real time using bispectral analysis. A suitable body surface electrode acquires the signal from a region of interest. The signal is then amplified, digitized, and transmitted to a host microcomputer where an arrhythmia-free QRST complex is chosen interactively. Using standard cross-correlation methods a suitable number of complexes are extracted from the record. The extracted complexes are used to compute bispectral parameters using a frequency domain or a parametric based approach. A reference clinical database is used to identify frequency pairs most sensitive to particular interventions or diagnostic states of interest. The values at these frequency pairs are then extracted from the patient's bispectral arrays. The ensemble of values for the particular diagnostic determination under consideration is used to compute a single value index which serves as the diagnostic criterion by which the patient's state is judged. In this way the quantification of nonlinear dynamic properties of the frequency structure of the QRST yields information about the presence and extent of coronary artery disease (CAD), myocardial ischemia, cardiac electrical stability, risk of malignant ventricular arrhydthmia, site(s) of origin of malignant arrhythmias, extent of malignancy of arrhythmias, degree of antiarrhythmic drug efficacy, neural and humoral inputs to the heart, pump function/ejection fraction, and ongoing organ rejection in cardiac transplant patients.

56 Claims, 24 Drawing Sheets

OTHER PUBLICATIONS

Barnett, T. P., Bispectrum Analysis of Electroencephalogram Signals During Walking and Sleeping.

Susumum, T., Analysis of Wave Shapes of Alphas Wave on EEG by Means of the Bispectrum.

Whitton, J. L., Genetic Dependence of the Electroencephalogram Bispectrum.

Raghuveer, M. R., Bispectrum Estimation: A Parametric Approach.

Teichholz, L. E. et al., The Cardiointegram: Detection of Coronary Artery Disease in Males with Chest Pain and a Normal Resting Electrocardiogram.

Simson, M., Use of Signals in the Terminal QRS Complex to Identify Patients with Ventricular Tachycardia After Myocardial Infarction.

Cain, M. E. et al., Fast-Fourier Transform Analysis of Signal-Averaged Electrocardiograms for Identification of Patients Prone to Sustained Ventricular Tachycardia.

Nolle, F. M., A Clincial Computer System for Monitoring EKG Rythm.

Nolle, F. M., et al., The ARGUS/H System for Rapid Analysis of Ventricular Arrhythmias.

Meade, C. N. et al., Argus Algorithm Development.

Oliver, G. C. et al., Detection of Premature Ventricular Contractions with a Clinical System for Monitoring Electrocardiographic Rhythms.

Balm, G., Crosscorrelation Techniques Applied to the Electrocardiogram Interpretation Problem.

Automatic Real Time Arrhythmia Monitoring in the Intensive Coronary Care Unit, American Journal of Cardiology.

Spitz, A.L. et al., Ambulatory Arrhythmia Quantification by a Correlation Technique.

Spitz, A. L. et al., Automated Family Classification in Ambulatory Arrhythmia Monitoring.

Drawing No.: 261101-873, Name: Pre Amp Iso.

Patient Safety, Hewlett-Packard.

Solar Cells Make Monitoring Safe.

Holmer, N. G. Isolation Amplifier Energized by Ultrasound.

Klijn, J. A., The Isolation Amplifier, An Interface Between EEG Recorder and Data Processor.

Moseley, H. et al., Removal of AC Interface from the Electrocardiogram.

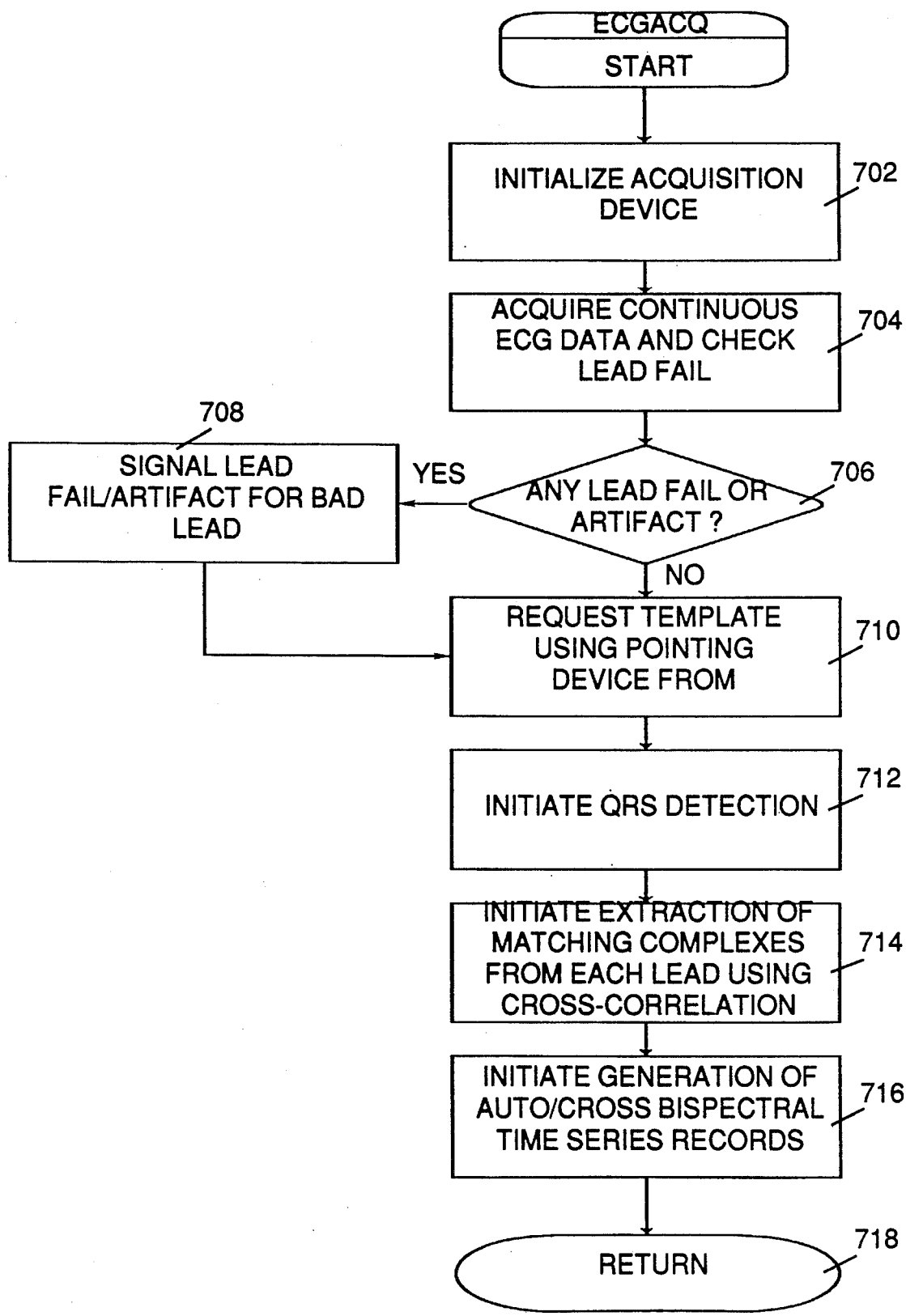

FIG. 14

Table 14(a).

| | | | |
|---|---|---|---|
| POJMH12A.BY | 12.25212670 | SOKHJ04A.BY | 21.26438900 |
| CADMJ06A.BY | 22.53816800 | TAREJ07A.BY | 24.04331400 |
| KIJHJ06A.BY | 25.05850220 | WEARH09A.BY | 25.50495530 |
| BREAA25A.BY | 25.78440280 | ROMAI20A.BY | 26.68617630 |
| LEGNJ07A.BY | 27.35936550 | AYDKJ17A.BY | 28.80974580 |
| KRRXA12A.BY | 29.20651050 | ALDAI15A.BY | 31.61214070 |
| GAKCI08A.BY | 33.26648710 | ALDSB23A.BY | 34.04255680 |
| CAJXH09A.BY | 34.30604170 | DERXJ11A.BY | 34.43464660 |
| SIJEJ07A.BY | 36.91619870 | LASPI20A.BY | 38.84684750 |
| PRDMI08A.BY | 41.32183460 | KIWWJ06A.BY | 42.58206940 |
| SIDSJ06A.BY | 46.49957660 | LUWJJ11A.BY | 47.29038240 |
| KRJLI27A.BY | 47.33069610 | DODXH25A.BY | 53.40213010 |
| LACJB23A.BY | 57.13722610 | LEKXI20A.BY | 62.86845780 |
| PLIMI08A.BY | 63.58295440 | DAMBH25A.BY | 66.79967500 |

Table 14(b).

| | | | |
|---|---|---|---|
| KERXD04A.by | 8.58777046 | KWWJB23A.BY | 8.90316200 |
| BREJB15A.BY | 8.91221237 | MARTK28A.BY | 10.16669940 |
| LEJJH09A.BY | 10.40363500 | TEMXA17A.BY | 10.51200770 |
| FERSC26B.BY | 10.70160010 | BEBLI13A.BY | 10.83960440 |
| NOJEJ06A.BY | 11.20124050 | SADJI12A.BY | 12.18137650 |
| TRPAD03A.BY | 12.62624550 | ROGAD18A.BY | 12.93428040 |
| COJXD14A.BY | 17.09865380 | ALNXA24A.BY | 18.85142710 |
| MEVRE03A.BY | 18.90387920 | RINWB14A.BY | 18.96992110 |

FIG. 16

Table 16(a).

| | | | |
|---|---|---|---|
| CAADD19A.BZ | 9.00820732 | SIVJA12A.BZ | 9.01792526 |
| MURJB01A.BZ | 9.25046730 | MEGBA03A.BZ | 9.52403450 |
| DOPTK09A.BZ | 9.76105309 | VIDAI13A.BZ | 9.92419147 |
| BEMGH19A.BZ | 11.27546310 | MCMCA06A.BZ | 11.95668320 |
| KIWFC29A.BZ | 12.02414040 | BEWJC06A.BZ | 12.22941110 |
| PEWJH03A.BZ | 12.96870710 | STJHJ04A.BZ | 13.52073860 |
| MOAHD05A.BZ | 14.15726660 | GPLEE18A.BZ | 14.76358320 |
| BLDHC13A.BZ | 14.86789700 | DEFGH18A.BZ | 15.59866910 |
| DULJB14A.BZ | 18.31387140 | THMLJ12A.BZ | 19.27793310 |
| BACLC29A.BZ | 19.73213200 | HABBD17A.BZ | 19.99048230 |
| MAEJD05A.BZ | 21.32853510 | PEFLC22A.BZ | 21.37274740 |
| SIFJA13A.BZ | 21.51948740 | BEJAB16A.BZ | 21.52597430 |
| SPCHK30A.BZ | 22.34267430 | BANSH23A.BZ | 22.57764820 |
| DAAXK29A.BZ | 22.79805180 | FRSDC22A.BZ | 22.90790940 |
| HAFLB08A.BZ | 24.19918440 | LEWXI15A.BZ | 25.14107320 |
| ALRWA12A.BZ | 25.26878550 | ALPRK22A.BZ | 25.82863240 |
| NOMPA18A.BZ | 34.38295360 | BERHD05A.BZ | 34.66892620 |
| BERJB21A.BZ | 40.08743670 | TRJFI13A.BZ | 46.21981050 |
| HOREB23A.BZ | 52.51377110 | | |

Table 16(b).

| | | | |
|---|---|---|---|
| DOMIB23A.BZ | 20.90007590 | LARCD05A.BZ | 29.86979290 |
| HEGDI15A.BZ | 31.09114650 | VASCD10A.BZ | 33.72085570 |
| GABMJ03A.BZ | 34.00053020 | TRVSA31A.BZ | 34.75869370 |
| MAEDL14A.BZ | 37.54197690 | DAHEB15A.BZ | 43.78262330 |
| GIRLL21A.BZ | 47.85096740 | HAWJE22A.BZ | 48.92345810 |
| BOJXC21A.BZ | 49.29041290 | PANHD12A.BZ | 61.22085570 |

CARDIAC BIOPOTENTIAL ANALYSIS SYSTEM AND METHOD

This application is a continuation-in-part application of co-pending U.S. Ser. No. 107,419 filed Oct. 9, 1987, which is also assigned to the assignee of the present application.

BACKGROUND OF THE INVENTION

The present invention relates to a high-frequency, high-resolution cardiac biopotential analysis apparatus and method, and more particularly to a microcomputer-based cardiac biopotential analysis apparatus for qualitatively determining in a noninvasive manner, cardiac phenomena that can be ascertained by analyzing cardiac electrical activity.

Cardiac biopotentials arise from the discharge of hundreds of thousands of electrically active cells. The signal detected at the body surface is a composite determined by different types of tissue, differing locations of that tissue, and the type of organization (or disorganization) of the wavefront of activation. When transmitted to the body surface the signal is altered in morphology and frequency content as a result of such factors as body fat, rib cage size, and position of the heart in relation to the lungs. All these variables lead to challenging signal processing problems.

Despite nearly a century of use, the conventional scalar electrocardiogram ("ECG") has major shortcomings. Its value for the diagnosis of coronary artery disease (CAD) is limited. It is very useful when there has been an antecedent myocardial infarct (MI) ("heat attack") which leads to localized fibrosis extensive enough to be detectable. In the absence of previous MI, the abnormalities induced by CAD in the resting ECG in an asymptomatic individual are of limited sensitivity and specificity.

The scalar ECG is of much greater value for the detection of active, ongoing ischemia. Monitoring of the ST segment during chest pain is a reliable indicator of cardiac ischemia and is used diagnostically when chest pain spontaneously presents itself or when chest pain is deliberately provoked for diagnostic purposes as in exercise stress testing. However even for this diagnostic application there occur significant numbers of false positives often requiring further, more expensive noninvasive tests (nuclear imaging) or invasive assessment through the use of cardiac catheterization and coronary angiography.

For the assessment of the risk of sudden cardiac death due to malignant ventricular arrhythmias the conventional ECG is of practically no use whatsoever. Twenty four hour continuous ambulatory monitoring of the scalar ECG ("Holter monitoring") is of some value in the minority of individuals with significant amounts of ventricular extrasystoles, but at considerable expense and inconvenience to the patient.

Advances in computer technology have led to attempts to improve the diagnostic information extracted from the surface ECG. One such approach is the cardiointegram (CIG) which has been used for the detection of coronary disease. This approach, as described in "The Cardiointegram: Detection of Coronary Artery Disease in Males with Chest Pain and a Normal Resting Electrocardiogram", *J. Electrocardiography.* 19(3): pp. 257-267 (1986), applies a process of integration over the various sections of the QRST signal thereby highlighting information about the interrelationships of positive to negative deflections from the ORS to the TO interval and T wave amplitude. Using this technique it has been shown that coronary artery disease can be detected from the resting, normal ECG with a sensitivity and specificity slightly less than exercise stress electrocardiography.

More recently Abboud et. al in "High Frequency Electrocardiography Using an Advanced Method of Signal Averaging for Non-Invasive Detection of Coronary Artery Disease in Patient with Normal Conventional Electrocardiogram", *Electrocardiography.* 19(4): pp. 371-380 (1986) showed that high frequency components of the ECG (150-250 Hz) averaged in the frequency domain after the fast-Fourier transform exhibited a characteristic "zone of reduced amplitude" in patients with CAD. The sensitivity of this technique was 75%. CIG had similar sensitivity.

A second area in which new computer based techniques have been applied to electrocardiography is in the detection of patients at risk for malignant ventricular arrhythmias and sudden cardiac death. Simson in "Use of Signals in the Terminal QRS Complex to Identify Patients with Ventricular Tachycardia After Myocardian Infarction", *Circulation.* 64(2): pp. 235-242 (1981) showed that signal averaging in the time domain reveals the presence of low amplitude high frequency deflections in the terminal portion of the QRS complex, so-called 'late potentials". These late potentials have been correlated with inducibility of serious arrhythmias in the electrophysiology (EP) lab and with an increased risk of sudden death during longterm follow up of survivors of heart attack. However, the detection of late potentials has a poor predictive accuracy due to the problem of false positive tests.

An alternative approach to the detection of risk for arrhythmia uses indices of the power spectrum of the signal averages QRS. Cain et al in "Fast-Fourier Transform Analysis of Signal-Averaged Electrocardiograms for Identification of Patients Prone to Sustained Ventricular Tachycardia", *Circulation.* 69(4): pp. 711-720 (1984) showed that this approach can distinguish arrhythmia patients from controls and correlates with inducibility of arrhythmias in the EP lab. Recent attempts to reproduce such results have met with varied success, due to fundamental problems in defining length of segment for FFT and in distinguishing the end of the QRS from noise. Haberl et. al in "Comparison of Frequency and Time Domain Analysis of Signal Averaged Electrocardiogram in Patients with Ventricular Tachycardia and Coronary Artery Disease: Methodologic Validation and Clinical Relevance. *JACC.* 12(1): pp. 150-158 (1988) applied successive FFTs that are shifted in time to the terminal portion of the signal averaged QRS to address some of the problems with the Cain method. Neither the time-domain indices of "late potentials" nor the power spectral indices of Cain or Haberl have been shown to be influenced by drugs. This has limited the application of these technologies to diagnostics, where the problem of false positives leads to their use as additional procedures at additional cost. Judgement of therapeutic efficacy continues to require additional costly invasive and noninvasive procedures.

The fundamental limitation of techniques applied to the ECG to date is their linear nature. The cardiac electrical signal is a complex summary of spatial and temporal inputs and many nonlinear dynamic features should be expected. In particular, neural inputs to the heart will have significant nonlinearities. What is true in health is at least equally true in disease. Thus a disease process can be expected to lead to characteristic alterations in nonlinear properties as well as linear ones. An ability to quantity abnormalities in nonlinear dynamics would therefore be expected to enhance diagnostic power and improve the assessment of therapeutic efficacy.

It is therefore a principal object of the present invention to provide a noninvasive system and method for reliably determining myocardian physiologic properties.

Another object of the present invention is to provide a noninvasive system and method for quantifying linear and nonlinear properties of phase and energy components within the frequency structure of the electrocardiogram.

A further object of the present invention is to provide a noninvasive system and method for diagnosing and quantifying coronary artery disease.

Another object of the present invention is to provide a noninvasive system and method for the detection and quantification of myocardial ischemia in real time, for example as a part of intraoperative monitoring.

Another object of the present invention is to provide a noninvasive system and method for the detection of successful reperfusion of the infarct-related artery in patients given thrombolytic therapy for acute myocardian infarction.

A further object of the present invention is to provide a noninvasive system and method for the assessment of coronary artery restenosis after successful percutaneous transluminal coronary angioplasty.

A further object of the present invention is to provide a noninvasive system and method for the quantification of cardiac electrical stability fixed or real time and the propensity for arrhythmias whether due to drugs, heart disease, or neural factors.

A further object of the present invention is to provide a noninvasive system and method for the quantification of the extent of malignancy of cardiac arrhythmias.

A further object of the present invention is to provide a noninvasive system and method for the identification of wide-complex supraventricular tachycardia from sustained vertricular tachycardia.

A further object of the present invention is to provide a noninvasive system and method for assessing the efficacy of therapy for arrhythmias and sudden cardiac death whether that therapy is drugs or surgery.

A further object of the present invention is to provide a noninvasive system and method for quantifying the effects of neural and humoral inputs to the heart, including the sympathetic and parasympathetic systems.

A further object of the present invention is to provide a noninvasive system and method for evaluating pump function and quantifying ejection fraction.

It is still another object of the present invention to provide a noninvasive system and method for quantifying the effects of ongoing organ rejection in cardiac transplant patients.

SUMMARY OF THE INVENTION

The cardiac biopotential analysis system and method of the present invention detects and quantifies the linear and nonlinear dynamic properties of cardiac depolarization and repolarization in a noninvasive manner. In so doing the invention provides a method for quantifying abnormalities in nonlinear dynamics and thereby enables without limitation the detection and quantification of coronary artery disease (CAD), myocardial ischemia, cardiac electrical stability, risk of malignant ventricular arrhythmia, site(s) of origin of malignant arrhythmias, extent of malignancy of arrhythmias, degree of antiarrhythmic drug efficacy, neural and humoral inputs to the heart, pump function/ejection fraction, and ongoing organ rejection in cardiac transplant patients.

A suitable electrode and amplifier system are used to acquire the cardiac electrical signal from the body surface of a region of interest. Very high frequency content is preserved by setting band pass filters at 0.05-512 Hz. Digital sampling is performed and digitized data is transmitted over a high speed serial line to a host microcomputer. A sinus QRST complex or a ventricular ectopic beat is chosen interactively as a template. Using standard crosscorrelation techniques a preselected number of complexes which match the template are extracted. Autobispectral or crossbispectral analysis is then performed using either an FFT approach or a parametric approach.

In autobispectral analysis a complex autotriple product array and a real autotriple product array is produced for a number of beats that match the preselected template. All of the autobispectral complex triple product arrays are then added point by point and divided by the total number of beats to create an average autobispectral complex triple product array. The autobispectral real triple product arrays are averaged in the same manner to create an average real triple product array. The magnitude of each averaged point in the complex autotriple product array is then divided by the square root of the real triple product array to form an autobiocoherence array. An autobiphase array can also be produced by deriving the arc tangent of the ratio of the imaginary to real part of the complex autotriple product array.

In the crossbispectral analysis a complex crosstriple product array and a real crosstriple product array is produced for a number of successive pairs of beats that match the preselected template. After averaging, the resultant average complex crosstriple product array and average real crosstriple product array are used to produce the crossbispectral density array, the crossbiocoherence array and the crossbiphase array.

Each of the generated bispectral arrays can contain up to (nfft/2+2)*nfft/8 data points if a nfft-point FFT is used. Although all, or nearly all of the values at these points can be expected to change from normal due to different interventions, drugs, or disease states, in the preferred embodiment only those points which show the greatest fidelity for tracking the diagnostic determination in question are utilized to create a diagnostic criterion. In the preferred embodiment the ensemble of points most sensitive to a particular intervention or physiologic process is used to create one or more clinically useful single value indices from the computed bispectral arrays. The indices are then used as diagnostic figures of merit for detection and quantification of coronary artery disease (CAD), myocardial ischemia, cardiac electrical stability, risk of malignant ventricular arrhythmia, site(s) of origin of malignant arrhythmias, extent of malignancy of arrhythmias, degree of antiarrhythmic drug efficacy, neural and humoral inputs to the heart, pump function/ejection fraction, and ongoing organ rejection in cardiac transplant patients. This approach makes it possible for any, even unskilled, operator to meaningfully interpret the output of the diagnostic device.

In situations where continuous monitoring is required, indices are continuously displayed on a video terminal enabling an operator to interactively evaluate regions of interest. For record keeping purposes index values and other pertinent variables can be sent to a hard copy output device or stored to magnetic storage device, such as a disk.

These and other objects and features of the present invention will be more fully understood from the following detailed description which should be read in light of the accompanying drawings in which corresponding reference numerals refer to corresponding parts throughout the several views.

BRIEF DESCRIPTION OF THE DRAWINGS

FIG. 7 is a flow chart of the process utilized by the system and method of the present invention for the acquisition of ECG data;

FIGS. 14(a)-14(b) are tables of the sample indices for normal subjects and for CAD subjects, respectively, generated by the system and method of the present invention in connection with the establishment of clinical reference arrays;

FIG. 16(a)-16(b) are tables of sample indices for MI subjects and VT/VF subjects respectively;

DETAILED DESCRIPTION OF THE PREFERRED EMBODIMENTS

Figure 1:
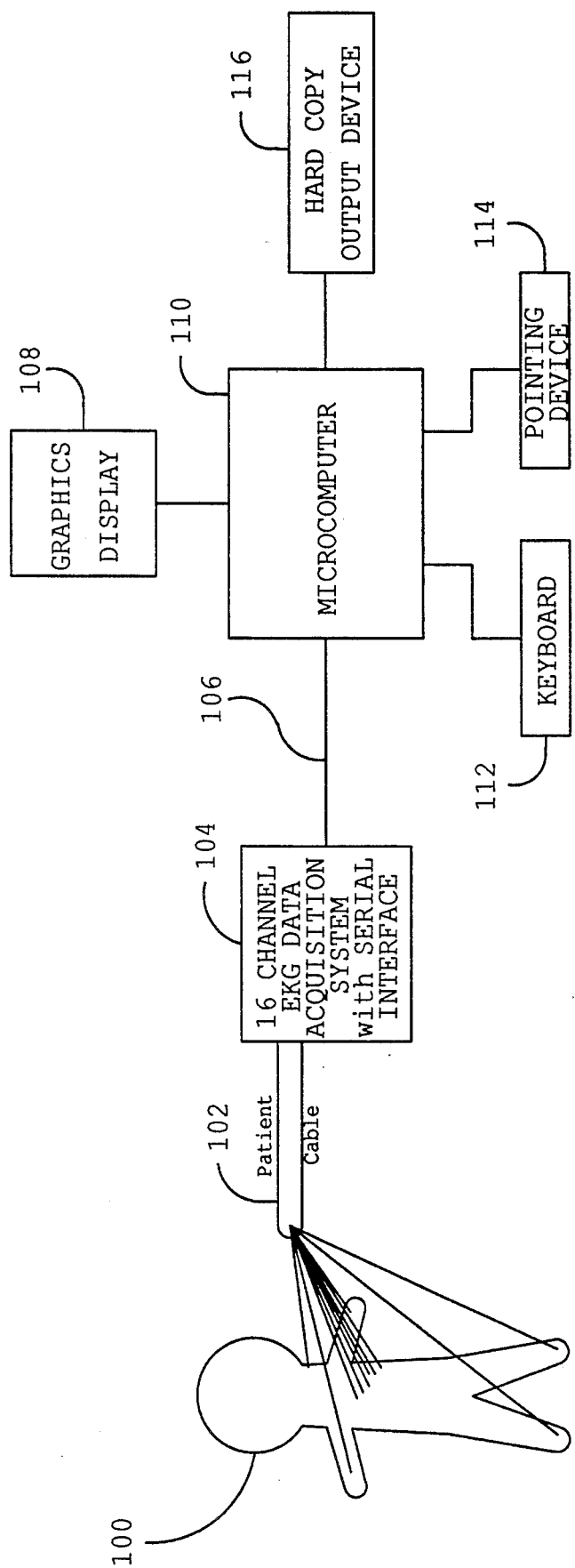
FIG. 1 is a schematic diagram of the components of the cardiac biopotential analysis system of the present invention.

Referring to FIG. 1, the apparatus of the present invention is connected to a patient 100 through a set of surface electrodes using a standard limb, precordial and orthogonal placement protocol. The ECG signals are picked up by the electrodes and transmitted over a patient cable 102 to a 16 channel ECG data acquisition system 104 with a serial interface.

The data acquisition system 104 filters, amplifies and digitizes the ECG waveforms and sends the digitized data to a microcomputer 110 via a high speed synchronous serial line 106. In addition, the serial line 106 can be used to download filtering, gain and sampling rate instructions to the data acquisition unit 104.

The microcomputer 110 process the serial data stream in order to generate all computed data arrays. These arrays are then used in conjunction with predetermining reference arrays derived from clinical studies to produce diagnostic indices which indicate the status of the patient. These indices are displayed on the graphics display 108. Printed output of the diagnostic index is also available on the hard copy output device 116 which is connected to the microcomputer 110. Interaction between the operator and the system is provided by means of a keyboard 112 and pointing device 114 with feedback on the graphics display 108.

Figure 2:
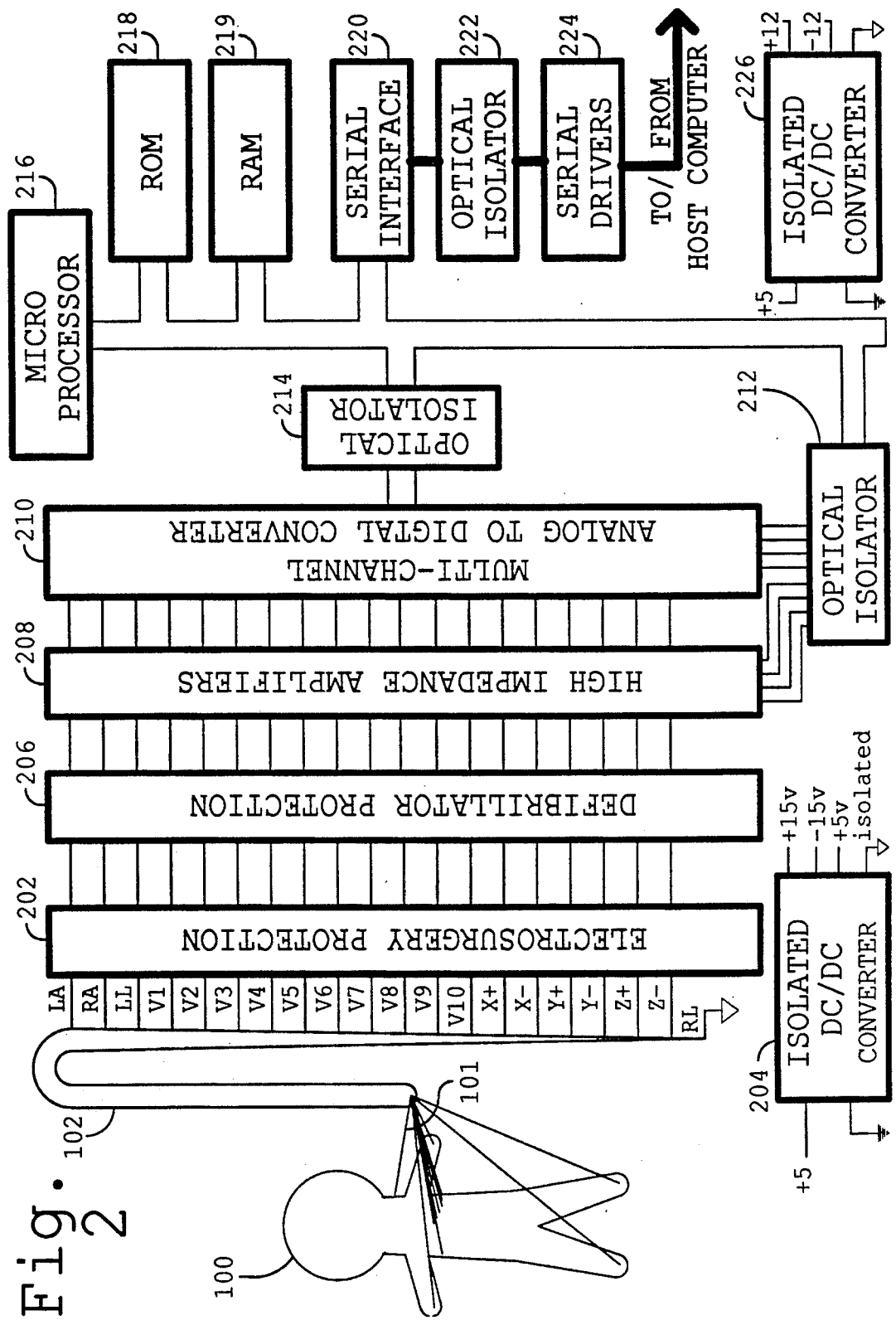
FIG. 2 is a schematic diagram of the 16 channel ECG data acquisition system, utilizing a serial interface, of the cardiac biopotential analysis system as shown in FIG. 1.

The 16 channel data acquisition system 110 is shown in greater detail in FIG. 2. The ECG surface potential, detected by a surface electrode mounted on the patient 100, passes through an electrosurgery protection circuit 202, a defibrillator protection circuit 206 and an amplifier/filter circuit 208 before being passed on to the multi-channel analog to digital converter 210.

The electrosurgery protection circuit 202 includes a radio frequency (rf) filter, which limits the rf current through the patient leads 101 to less than 100 micro amperes and thus protects the patient 100 from rf burns and protects the amplifiers 36 from damage resulting from exceeding the absolute maximum input voltage specified by the manufacturer. This circuit can be an LC section circuit consisting of a generic inductor connected in series to a generic capacitor which is then connected to ground.

The defibrillator protection circuit 206 limits the voltage to the amplifiers 208 to a safe level when a defibrillator is applied to the patient 100 and discharged. This circuit preferably includes a neon light bulb and/or a parallel variable resistor connected in series to a grounded resistor.

The amplifier/filter circuitry 208 is controlled by a microprocessor 216 for default gain and filtering levels or alternate gain and filtering levels as requested by the operator. Preferred gain and filtering settings are discussed below. This circuitry 208 includes three stages: the first is a pre-amplifier stage that can be assembled using a wide variety of high impedance pre-amplifiers such as those sold by National Semiconductor, Sunnyvale Calif.; the second is a programmable filters stage which can utilize filters sold by Frequency Devices, Haverhill Mass.; the third stage is a programmable amplifiers stage which can be assembled from operational amplifiers used in conjunction with a multiplying digital to analog (D/A) converter, both of which components are available from National Semiconductor. The multiplying D/A is used to set the gain to the appropriate levels requested by the microprocessor 216.

The high impedance pre-amplifier of each channel will saturate to either the positive or negative supply voltage if the input of the pre-amplifier is not terminated. This will lead to large positive value or a large negative value at the output of amplifier section 208. Such values will be used to identify lead failure.

The output of all 16 channels of the amplifier/filter 208 is fed to a multi-channel analog to digital converter (A/D) 210 which is under microprocessor 216 control for sampling rate settings. The analog signals are converted to digital data format suitable for input to a computer. A/D converters sold by Analog Devices, Norwood, Mass. can be used for this purpose.

The multi-channel A/D converter 210 is optically coupled to data bus 215 by optical isolator 214. All control lines to the amplifiers/filters 208 and the A/D convertor 210 are also optically isolated by optical isolator 212. Any known optical isolators can be used for this purpose.

All DC power lines going to the amplifiers/filters 208 and A/D convertor 210 are also isolated from the AC power line with a DC/DC convertor 204 in order to provide complete patient isolation from ground. DC/DC converters available from Burr Brown can be used for this purpose.

The basic instructions for controlling operation of the microprocessor 216 are stored in a read only memory (ROM) 218. The random access memory (RAM) 219 is used as a buffer memory for data, and a portion of the RAM 219 can also be used as program memory when a control program is being downloaded from the microcomputer 110.

Serial interface 220 operates under the control of the microprocessor 216. The serial interface 220 is optically coupled with optical isolators 222 to high speed synchronous serial drivers 224 to provide a synchronous serial link 106 between the 16 channel data acquisition system 104 and any compatible high speed synchronous serial interface card on any computer. The serial lines are isolated by optical isolators 222 and DC/DC convertor 204 to provide increased patient safety and to protect the host computer 110 from any transients.

Figure 3:
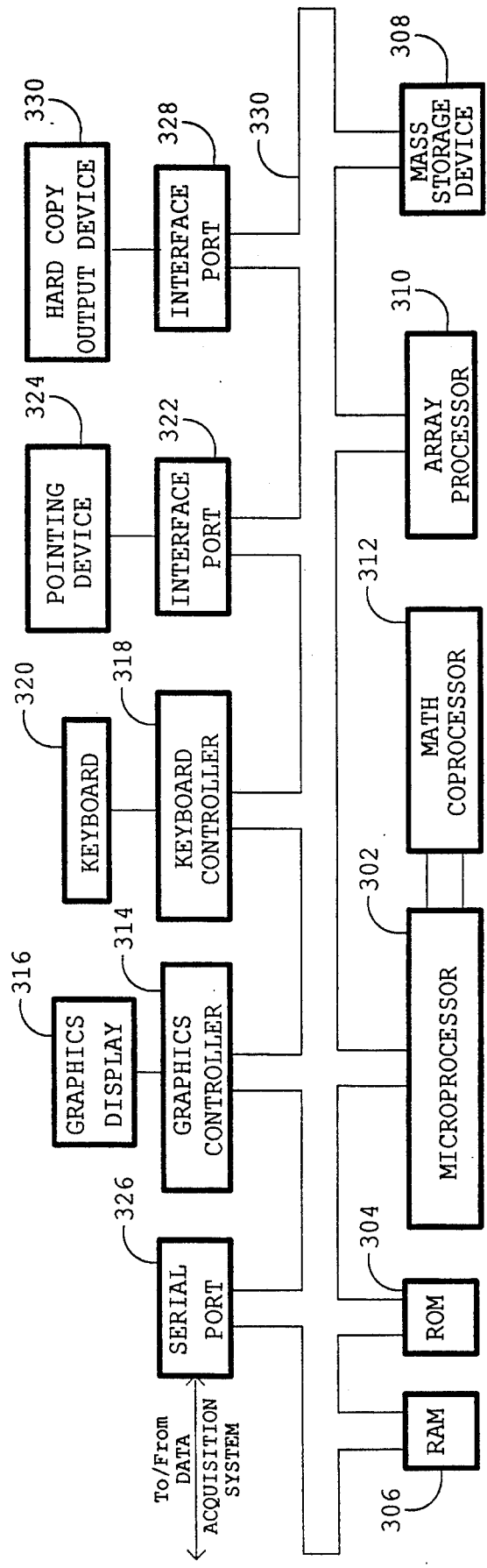
FIG. 3 is a schematic diagram of the microcomputer utilized by the cardiac biopotential analysis system of FIG. 1.

The host or microcomputer 110 of FIG. 1 is shown in greater detail in FIG. 3. The entire microcomputer system runs under control of a microprocessor 302 with the program memory for the microprocessor being stored in ROM 304. The RAM 306 is used for storage of intermediate data. The mass storage device 308 is used for storing clinical databases as well as archiving patient data.

In a preferred embodiment, the microcomputer 110 contains an array processor 310 (such as the Vortex sold by SKY of Lowell, Mass.) on which complex arithmetic calculations can be performed on entire arrays of data dimultaneously. The preferred embodiment also includes a math coprocessor 312 which is connected directly to microprocessor 302. The math coprocessor 312 is used for scalar and graphic calculations while the array processor 310 is used to calculate bispectral and other data vectors.

A graphics controller 314 operating under program control of the microprocessor 302 drives a graphics display 316. A keyboard controller 318 interfaces directly with the operator's keyboard 320. An interface port 322 is provided for the pointing device 324.

Operator control of the entire acquisition, analysis and display procedure is controlled from the keyboard 320 and pointing device 324 with feedback on the graphics display 316. One high speed synchronous serial port 326 is provided to interface with the 16 channel data acquisition system 104. Port 326 can be used to send control data to the system (e.g., filtering, gain, sampling rate, start/stop acquisition, perform self diagnostics) and to receive ECG data from the system, as well as to download program data to the system. Another serial or parallel interface port 328 is provided to drive a hard copy output device 330 for printing desired diagnostic indices.

Figure 4:
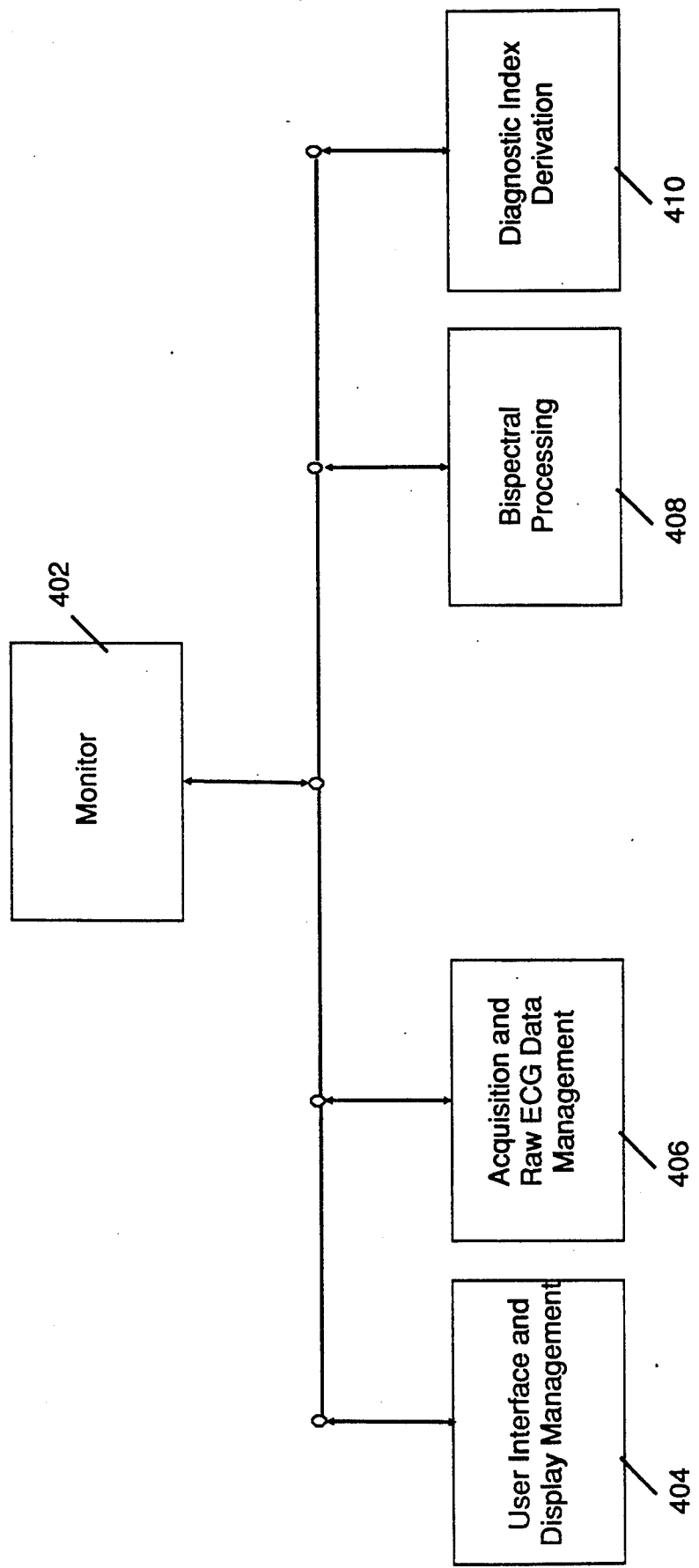
FIG. 4 is a block diagram of the interaction of the various tasks performed by the system and method of the present invention.

Referring now to FIG. 4, the functions performed by the system and method of the present invention will now be described. As mentioned above, the system and method of the present invention quantify linear and nonlinear properties of phase and energy components within the frequency structure of the ECG from a preselected number of leads. Diagnostic indices are then generated from the bispectral data arrays by utilizing predetermined reference arrays. The indices are used for the quantification of coronary artery disease (CAD), myocardial ischemia, cardiac electrical stability, risk of malignant ventricular arrhythmia, site(s) of origin of malignant arrhythmias, extent of malignancy of arrhythmias, degree of antiarrhythmic drug efficacy, neural and humoral inputs to the heart, pump function/ejection fraction, and ongoing organ rejection in cardiac transplant patients.

The monitor module 402, handles the overall operations of the system via integration of data and process information from the user interface module 404, acquisition and raw ECG data management module 406, bispectral processing module 408 and diagnostic index derivation module 410. A detailed description of the operation of module 402 will be provided below in connection with the description of FIG. 5.

The user interface and display management module 404 represents the means through which the operator controls and interacts with the system during the course of a procedure. This includes, but is not limited to, entry of information regarding the patient, type of diagnostic procedure being carried out, lead and acquisition settings; continuous display of acquisition status, lead integrity, display of diagnostic indices; and requests for printing and archiving results to disk. Module 404 directly interacts with the monitor module 402. The operations handled by module 404 can be achieved under one of many commercially available environments such as Microsoft's Windows.

The acquisition and raw ECG data management module 406, handles all of the raw ECG data checking and processing prior to bispectral analysis. This includes, but is not limited to, continuous acquisition of ECG data and the verification of the integrity of the data; performing QRS detection; performing crosscorrelation with the preselected template to identify suitable complexes; extracting suitable complexes from leads of interest in preparation for autobispectral and crossbispectral processing. Module 405 directly interacts with the monitor module 402, and a more detailed description of module 406 will be provided below in connection with the description of FIG. 7.

The bispectral processing module 408 controls the generation of all data arrays measuring dynamic phase and energy properties within the ECG. This information can be organized in both autobispectral and crossbispectral arrays utilizing either an FFT based on parametric based approach. The tasks include, but are not limited to, nonlinear/exponential transform of the signal, Fourier transformation, the generation of power spectrum, autobispectral density, crossbispectral density, autobicoherence, crossbicoherence, autobiphase, and crossbiphase. Module 408 directly interacts with the monitor module 402, and a more detailed description of module 408 is provided below in connection with FIGS. 9 and 10.

The diagnostic index derivation module 410 generates the data values utilized in the diagnostic process. The task includes, but is not limited to, identifying frequency pairs of interest through the use of predetermined clinical reference arrays and creating a diagnostic index from the values in the bispectral data arrays at the frequency locations defined by the reference array. Module 410 directly interacts with the monitor module 402, and more detailed description of module 410 is provided below in connection with FIG. 12.

Figure 5:
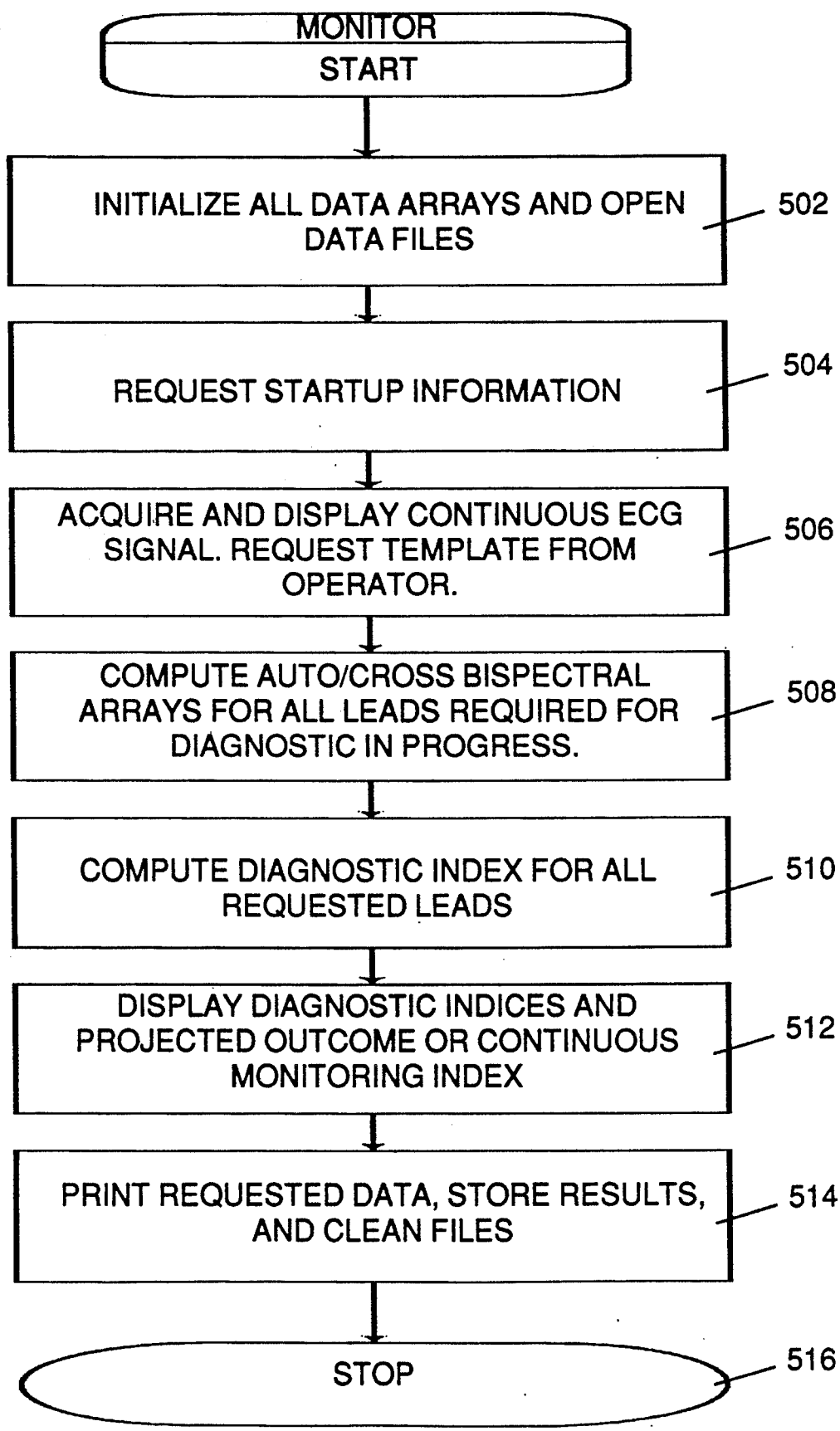
FIG. 5 is an overview flow chart of the operation of the system and method of the present invention.

Referring to FIG. 5, the operation of the monitor module 402 will now be discussed. In step 502, the data arrays used to store the digitized raw ECG and the bispectral data of each lead are initialized. The data files required for storage and files containing databases required for the computation of diagnostic indices are also opened in the initializing step 502.

In step 504 the system requests the information required to start the acquisition and diagnostic process from the user via the user interface module. This information includes the type of diagnostic procedure to be conducted and any operator requested modification to the system defaults such as leads used, clinical databases to access for diagnostic index computation, filtering, gain and sampling rate information for each lead. The type of diagnostic procedure as entered by the operator will be used by the system to inform the operator of the lead placement protocol required, and the type of templates to be selected (sinus rhythm or ectopic beat). The system will also use the type of diagnostic procedure it will perform to select the portion of the complexes to be used as time series for bispectral processing as well the type of bispectral arrays that need to be computed for use in conjunction with the predetermined clinical databases to yield a final diagnosis. The process of identifying the most effective leads for a particular diagnostic procedure and the generation of the clinical databases will be discussed later.

In step 506, ECG signals are continuously acquired and displayed from the leads needed for the diagnostic operation being performed. All channels transmitting artifactual data are properly signaled to the operator to correct the problem. While using the pointing device, the operator is requested to select a suitable template against which incoming ECG complexes are matched.

The system, in step 508, computes the necessary autobispectral and crossbispectral arrays required by the databases for the generation of the diagnostic indices requested by the operator.

In step 510, the diagnostic indices from all generated autobispectral and crossbispectral arrays are computed. Autobispectral density and crossbispectral density clinical reference arrays are utilized in these diagnostic index computations. In the case of a static one time diagnostic determination, such as detecting of CAD, the system displays, in step 512, the resultant diagnostic indices and a projected outcome based on information from the clinical databases. In the case of monitoring an ongoing cardiac process such as intraoperative ischemia the index is displayed continuously over time during the course of the procedure requiring it.

In step 514, requested printouts are produced, results are stored to disk for archival purposes and all files are closed. In step 516, the process is terminated.

Figure 6:
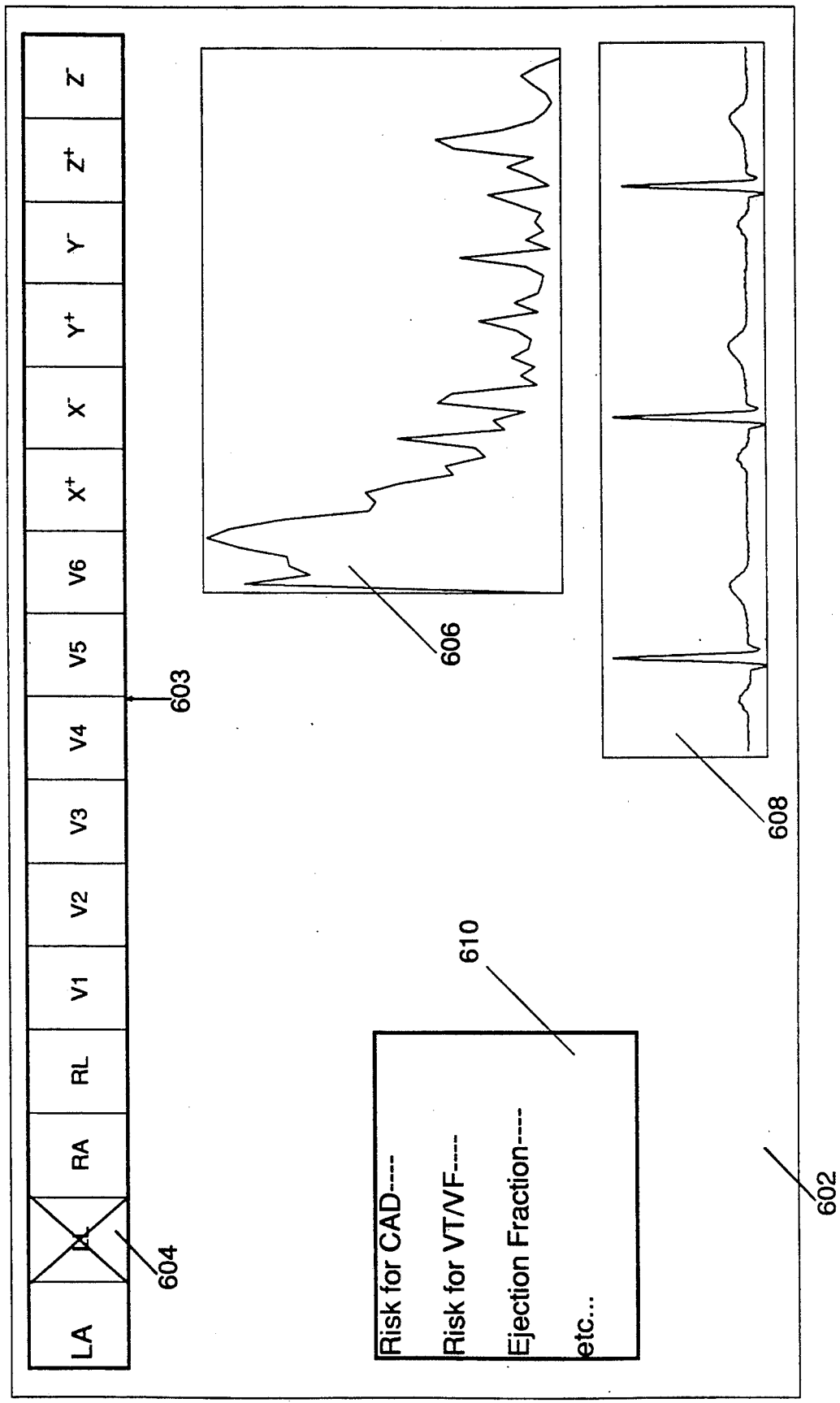
FIG. 6 is a representation of the output provided by the system and method of the present invention.

A sample display representation generated by the system is shown in FIG. 6. The top section of the screen 602 is divided into 16 sections 603 each representing the region probed by an electrode. Each section will be covered by a large "X" 604 if lead fail or artifact was detected from the lead corresponding to that section.

A second portion of the screen 606 can be assigned to the continuous display of the diagnostic index if the system is being used in monitoring mode. The background of that portion is color coded to reflect the possible values allowed for in the range of the selected diagnostic index. The most current value of the diagnostic index will indicate what color is displayed in the background (e.g. Red=lowest value to Green=highest value). This will facilitate the examination of the patient's status at a distance.

A third portion of the screen 608 can be assigned to displaying one or several of the raw ECG data leads that is being acquired for processing. This will also provide for easy template selection using the pointing device.

A fourth portion of the screen 610 can be assigned to displaying the results of a static diagnostic test if the system is being used in that mode of operation.

Referring to FIG. 7, the acquisition and raw ECG data management module 406 will now be described in greater detail. In step 702, the acquisition system 104 is programmed with requested filtering, gain, sampling rate, and lead selection information.

In step 704, the acquisition system 104 acquires continuous ECG data for all requested leads and transfers this data to the host computer 110. The acquisition system 104 detects lead failures during the acquisition cycle, and in step 706, the acquired data is examined for lead failure signals and for the presence of artifact. In step 708, leads generating fail signals and/or artifactual data are marked for the monitor module 402.

In step 710, the system requests the operator to identify a template from the incoming data stream using the pointing device. In step 712, QRS detection is performed on the ECG data using any publicly available QRS detection program such as the algorithm disclosed by Engelese et al in "A Single Scan Algorithm for QRS-Detection and Feature Extraction, *IEEE Computers in Cardiology* (1979). Then in step 714, the system initiates continuous extraction of complexes that match the template from the incoming ECG data from each lead using standard cross-correlation techniques.

Depending on the diagnostic test requested by the operator and based on information from the clinical databases, bispectral processing will be performed on the full complex that matches the template or a portion of that complex. Also, depending on the test to be performed the complex can be a sinus rhythm beat or an ectopic beat. In step 716, the auto/cross bispectral time records are continuously generated by extracting a portion suitable for the diagnostic test from each matched complex from each of the leads required for the test. Each portion is assigned to an $X_i(t)$, where $X_i(t)$ are the individual time series records provided for autobispectral processing. Also in step 716, $Y_i(t)$ is set to $X_{i+1}(t)$ (the successive complex in the same lead) where $Y_i(t)$ are the time series records (in addition to $X_i(t)$) required for crossbispectral processing within the same lead. $Y_i(t)$ can also assume the value of a corresponding $X_i(t)$ from another lead providing for crossbispectral analysis between two leads. It should be noted that for autobispectral analysis $Y_i(t)$ is set to equal $X_i(t)$ and in all cases the index i denotes the record number from 1 to k, and where k is the number of bispectral averages computed.

Once the acquisition process is initiated the program will continuously pass to the monitor module (via interrupt handlers) raw time series data until the diagnostic test is completed. The program returns control to the monitor module 402 in step 718.

Figure 8A:
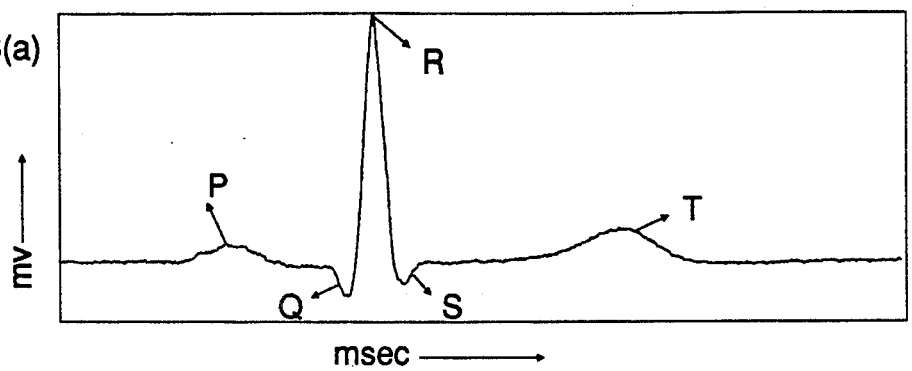
FIG. 8(a) is a diagram of a sample PQRST complex utilized by the system and method of the present invention.
Figure 8B:
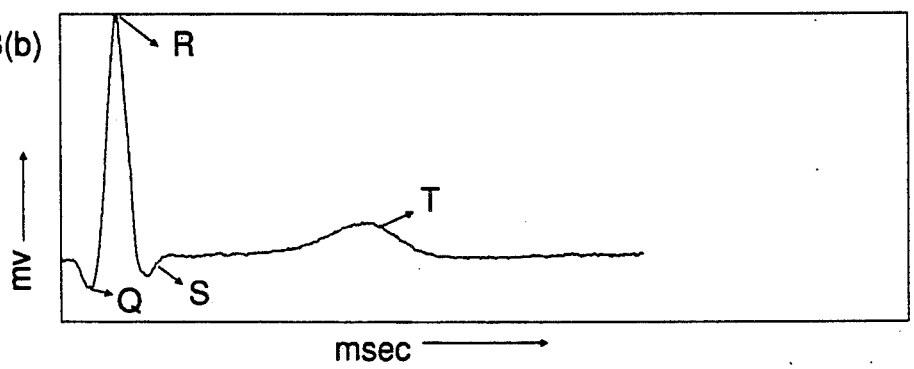
FIGS. 8(b)-8(d) are diagrams of possible extraction templates utilized for bispectral analysis by the method and system of the present invention.
Figure 8C:
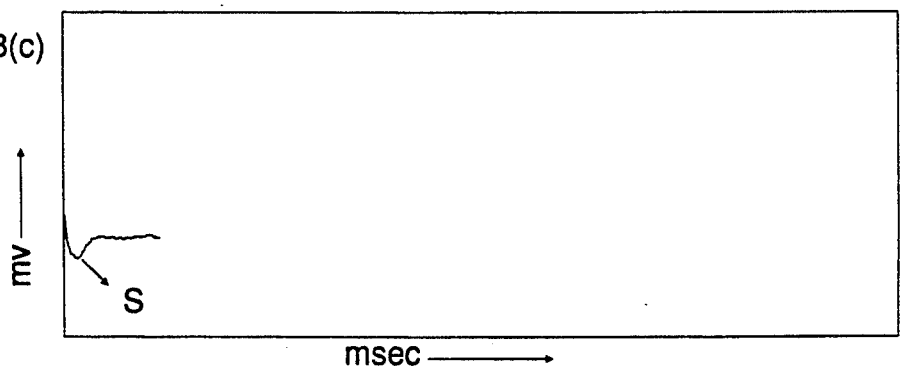
Figure 8D:
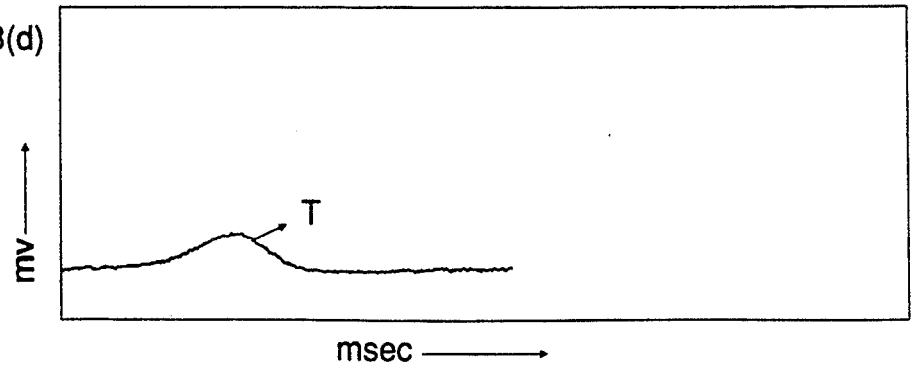

Now turning to FIG. 8, FIG. 8(a) shows a sample PQRST template, FIG. 8(b) shows the QRST portion extracted for processing; FIG. 8(c) shows the terminal part of the QRS extracted for processing; and FIG. 8(d) shows the ST segment with the T wave extracted for processing. The axes in FIGS. 8(a)–8(d) are not calibrated and the figures are for illustration purposes only.

Figure 9:
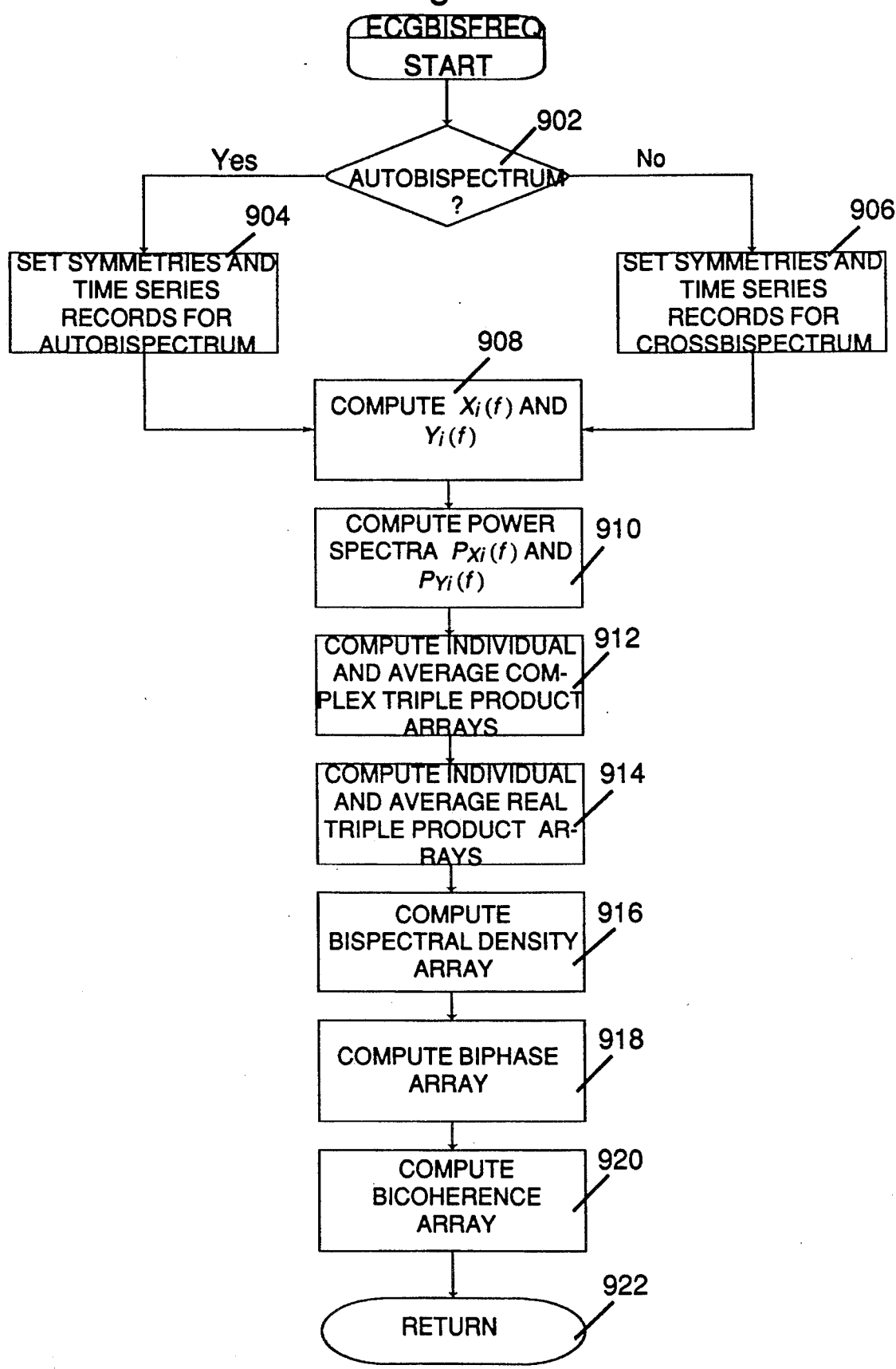
FIG. 9 is a flow chart of the frequency domain based steps for producing the autobispectrum or the crossbispectrum used by the system and method of the present.

Referring now to FIG. 9, the frequency domain based procedures for producing the autobispectrum or the crossbispectrum will now be discussed. In step 902, the system checks whether the computation to be performed is an autobispectral or crossbispectral computation. Autobispectral analysis is a special case of crossbispectral analysis and therefore different rules of symmetry apply.

In step 904, the system sets the following symmetries in order to proceed with autobispectral computation:

$$f_1+f_2<N/2$$

where N is the number of samples in the time series to be processed. N will depend on the length of the portion of the complex (in msec) and the sampling rate. For illustration purposes we will utilize the QRS portion of the selected complex with length of 160 msec. Since the sampling rate is 1024 samples/sec N will be equal to 160 samples or 1024 Hz.

$$0<f_2<f_1$$

$$X_i(t)=Y_i(t) \rightarrow X_i(f)=Y_i(f)$$

where $f_1$ and $f_2$ (also referred to as $F_1$ and $F_2$ or Frequency 1 and Frequency 2) denote the frequency pairs over which bispectral computation will be carried out, $X_i(t)$ and $Y_i(t)$ denote the individual time series records used for bispectral computation, $X_i(f)$ and $Y_i(f)$ denote the Fourier transform of the time series records and i denotes the record number which in this embodiment ranges from 1 to k.

In step 906, the following symmetries are adhered to for crossbispectral analysis:

$$f_1+f_2<N/2$$

$$0<f_1<N/2$$

$$0<f_2<N/2$$

$$-2f_2<f_1$$

$$X_i(t) \neq Y_i(t) \rightarrow X_i(f) \neq Y_i(f)$$

where all variables represent the same values as they do for autobispectral analysis, except that for crossbispectral analysis $X_i(t)$ and $Y_i(t)$ represent individually derived time series records where $Y_i(t)=X_{i+1}(t)=X_i(t)$ from a different lead providing for inter-lead crossbispectral analysis.

In step 908, the Discrete Fourier transform (DFT) $X_i(f)$ and $Y_i(f)$ of each record of the k selected records, is computed using a standard IEEE library routine or any other publicly available routine in step 908.

In step 910, the power spectra $P_{xi}(f)$ and $P_{yi}(f)$ of each record of the k selected records is computed by squaring the magnitudes of each element of the Fourier transform $X_i(f)$ and $Y_i(f)$ respectively.

The system computes the average complex triple product in step 912 by utilizing the following equations where $bc_i(f_1,f_2)$ is an individual complex triple product from one record and $BC(f_1,f_2)$ is the average complex triple product over all records:

$$bc_i(f_1,f_2)=X_i(f_1)*Y_i(f_2)*Y_i*(f_1+f_2)$$

where $Y_i*(f_1+f_2)$ is the complex conjugate of $Y_i(f_1+f_2)$.

$$BC(f_1,f_2)=\frac{1}{k}\sum_{i=1}^{k}bc_i(f_1,f_2)$$

The average real triple product is computed in step 914 by using the following equations where $br_i(f_1,f_2)$ is an individual real triple product from the one record and $BR(f_1, f_2)$ is the average real triple product over all records:

$$br_i(f_1,f_2)=P_{xi}(f_1)*P_{yi}(f_2)*P_{yi}(f_1+f_2)$$

$$BR(f_1,f_2)=\frac{1}{k}\sum_{i=1}^{k}br_i(f_1,f_2)$$

In step 916, the auto/crossbispectral density array $(BD(f_1,f_2))$ is computed using the following equation:

$$BD(f_1,f_2)=|BC(f_1,f_2)|$$

In step 918, the system computes the auto/crossbiphase array $(\phi(f_1, F_2))$ using the following equation:
$$(\phi(f_1,f_2)=\tan^{-1}[Im(BC(f_1,f_2))/Re(BC(f_1,f_2))]$$

$$0<\phi<2\pi \text{ (radians)}$$

In step 920, the system computes the auto/crossbicoherence array $(R(f_1,f_2))$ using the following equation:

$$R(f_1,f_2)=BD(f_1,f_2)/[BR(f_1,f_2)]^{\frac{1}{2}}$$

$$0<R<1$$

In step 922, the system returns the requested auto/-cross bispectral density, average real triple product, biocoherence, and biphase arrays to the monitor module 402.

Figure 10:
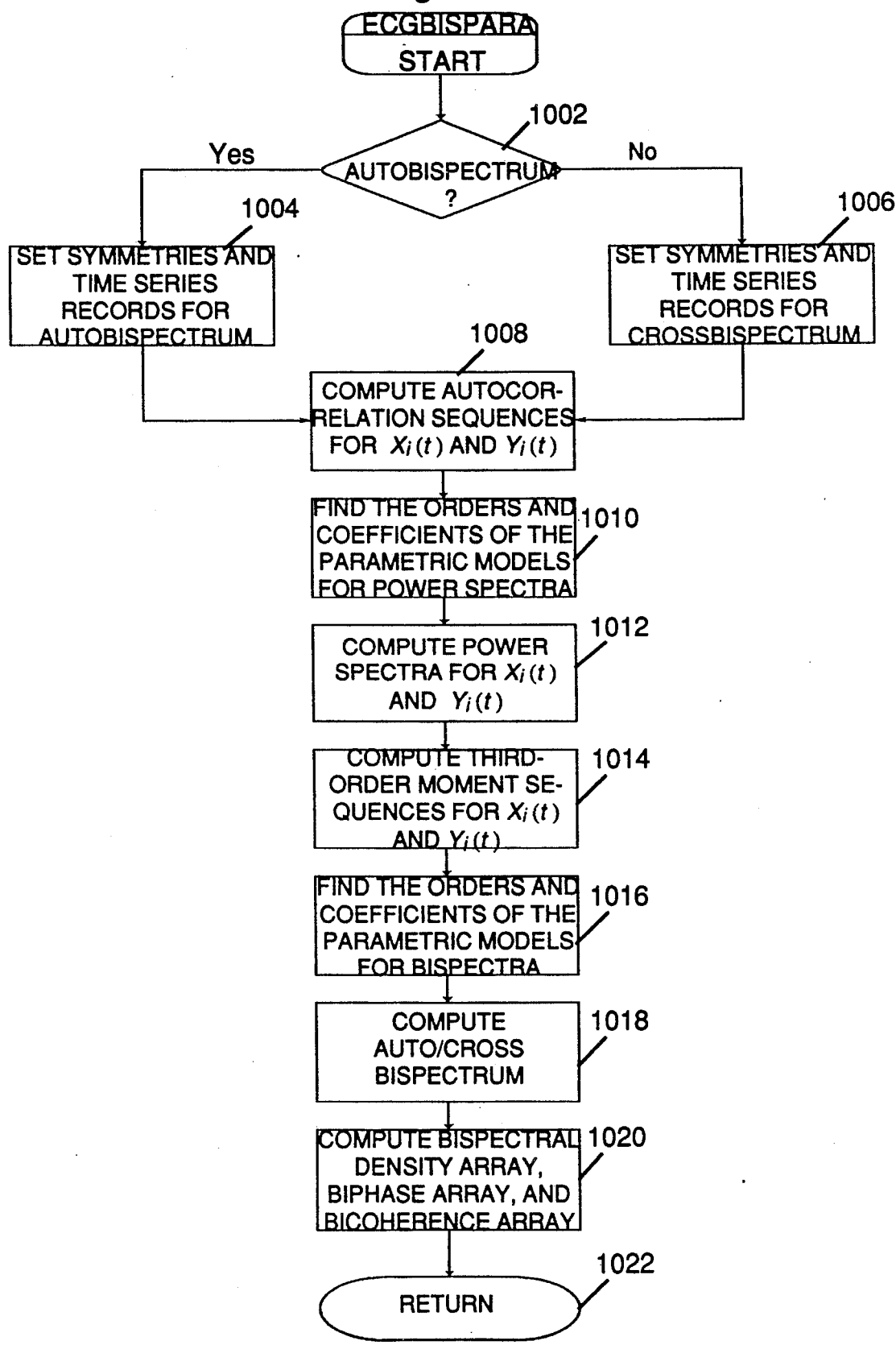
FIG. 10 is a flow chart of the parametric based steps for producing the autobispectrum or the crossbispectrum used by the system and method of the present invention.

Now turning to FIG. 10, a parametric based method for producing the autobispectrum and the crossbispectrum will now be described. In steps 1002, 1004, and 1006 the system sets the symmetries and time series records in the same manner as described above in steps 902, 904, and 906, respectively. The power spectra of $X_i(t)$ and $Y_i(t)$ are estimated in steps 1008, 1010, and 1012. This estimation method includes two major stages, the autoregressive (AR) model order selection and the power spectrum computation for $X_i(t)$ and $Y_i(t)$. In step 1008, the system computes two sequences of autocorrelations, $\{R_{2X}(m)\}$ and $\{R_{2Y}(m)\}$ using the following equation.

$$R_{2z}(m) = \frac{1}{M*N} \sum_{i=1}^{M} \sum_{t=0}^{N-|m|} z_i(t)z_i(t+m),$$

$$m = 0, 1, \ldots, L, z_i = X_i, Y_i$$

where M is the number of records (k in our case), and N is the number of samples per record (160 in our case). L is much greater than the possible AR filter order (we choose 50).

The Final Prediction Errors, $FPE_X(m)$ and $FPE_Y(m)$ respectively are chosen to be the orders of the AR filters of power spectra of $X_i(t)$ and $Y_i(t)$ respectively, i.e., $$FPE_X(Q_X) = \min \{FPE_X(m)\}$$

and $$FPE_Y(Q_Y) = \min \{FPE_Y(m)\}$$

Once the orders of the AR filters for power spectra are chosen, the autocorrelation sequences, $\{R_{2X}(m)\}$ and $\{R_{2Y}(m)\}$, are entered into Levinson recursion with order $Q_X$ and $Q_Y$, respectively, instead of L. The coefficient, $\{c_{iX}, i=0, 1, \ldots, Q_X\}$ and $\{c_{iY}, i=0,1,\ldots,Q_Y\}$, obtained from the recursion are the coefficients of the AR filters for power spectra of $X_i(t)$ and $Y_i(t)$ respectively. Then, in step 1012, the power spectrum, $P_z(f)$, is computed as the prediction error $(O_z^2)$ divided by square of the magnitude of the Fourier transform of the coefficients, i.e., $$P_z(f) = \frac{\sigma_z^2}{\left|1 + \sum_{i=1}^{Q_z} c_{iz} e^{-j2\pi f i}\right|^2}, z = X, Y.$$

The system estimates the auto/cross bispectrum in steps 1014, 1016, and 1018. The estimation process includes two major stages: the order selection and bispectrum computation. In step 1014, two sequences of third-order moments, $\{R_{3X}(\tau)\}$ and $\{R_{3Y}(\tau)\}$ are computed using the following equation.

$$R_{3z}(\tau) = \frac{1}{y*N} \sum_{i=1}^{y} \sum_{t=s_1}^{s_2} z_i(t)z_i^2(t+\tau),$$

$$z = X, Y, \text{ and } \tau = -L, \ldots, L$$

where $S_1 = \max(1, 1-\tau)$, $s_2 = \min(N, N-\tau)$, and L is much greater than the possible AR filter orders (e.g. 50).

In step 1016, two super matrices $T_X$ and $T_Y$ are formed as follows.

$$T_z =$$

$$\left\{ \begin{array}{cccc} R_{3z}(-L) & R_{3z}(-L+1) & \ldots & R_{3z}(0) \\ R_{3z}(-L-1) & R_{3z}(-L) & \ldots & R_{3z}(-1) \\ . & . & \ldots & . \\ R_{3z}(-2L) & R_{3z}(-2L+1) & \ldots & R_{3z}(-L) \end{array} \right\}, z = X, Y.$$

From the assumption we made about the AR filter of bispectrum, the orders $O_X$ and $O_Y$ of the AR filters of bispectra of $X_i(t)$ and $Y_i(t)$ and the ranks of the super matrices $T_X$ and $T_Y$. Therefore, $O_X$ and $O_Y$ are chosen by using singular value decomposition. Having found the orders, we obtain the coefficients of the AR filters of bispectra by solving the following linear system of equations:

$$\begin{pmatrix} R_{3z}(0) & R_{3z}(1) & \ldots & R_{3z}(O_z) \\ R_{3z}(-1) & R_{3z}(0) & \ldots & R_{3z}(O_z-1) \\ . & . & \ldots & . \\ R_{3z}(-O_z) & R_{3z}(-O_z+1) & \ldots & R_{3z}(0) \end{pmatrix} \begin{pmatrix} 1 \\ b_{1z} \\ . \\ b_{O_z z} \end{pmatrix} =$$

$$\begin{pmatrix} \beta_z \\ 0 \\ . \\ 0 \end{pmatrix}, z = X, Y.$$

where the skewness $(\beta_z)$ and the coefficients $(b_{1z}, \ldots, b_{O_z z})$, $z = X, Y$, can be obtained by solving the linear system of equations.

The auto/cross bispectrum of $X_i(t)$ and $Y_i(t)$ are computed in step 1018 as the cubic root of the triple product of the skewnesses $(\beta_X \beta_Y \beta_Y)^{\frac{1}{3}}$ divided by the triple product of the Fourier transforms of the AR filter coefficients $(H_z(f))$, i.e., $$BC(f_1, f_2) = (\beta_X \beta_Y \beta_Y)^{\frac{1}{3}} / H_X(f_1) H_Y(f_2) H_Y^*(f_1+f_2)$$

$$H_z(f) = 1 + \sum_{i=1}^{O_z} b_{iz} e^{-j2\pi f i}, z = X, Y.$$

and $BR(f_1, f_2)$ is the real triple produce for that same lead:

$$BR(f_1, f_2) = P_X(f_1)*P_Y(f_2)*P_Y(f_1+f_2)$$

After obtaining power spectrum and auto/cross bispectrum, the system computes the bispectral density array, the biphase, and the bicoherence in step 1020 the same way as in steps 916, 918, 920. In step 1022, the system returns to the monitor module 402 the requested bispectral density, biphase, and bicoherence arrays.

Figure 11A:
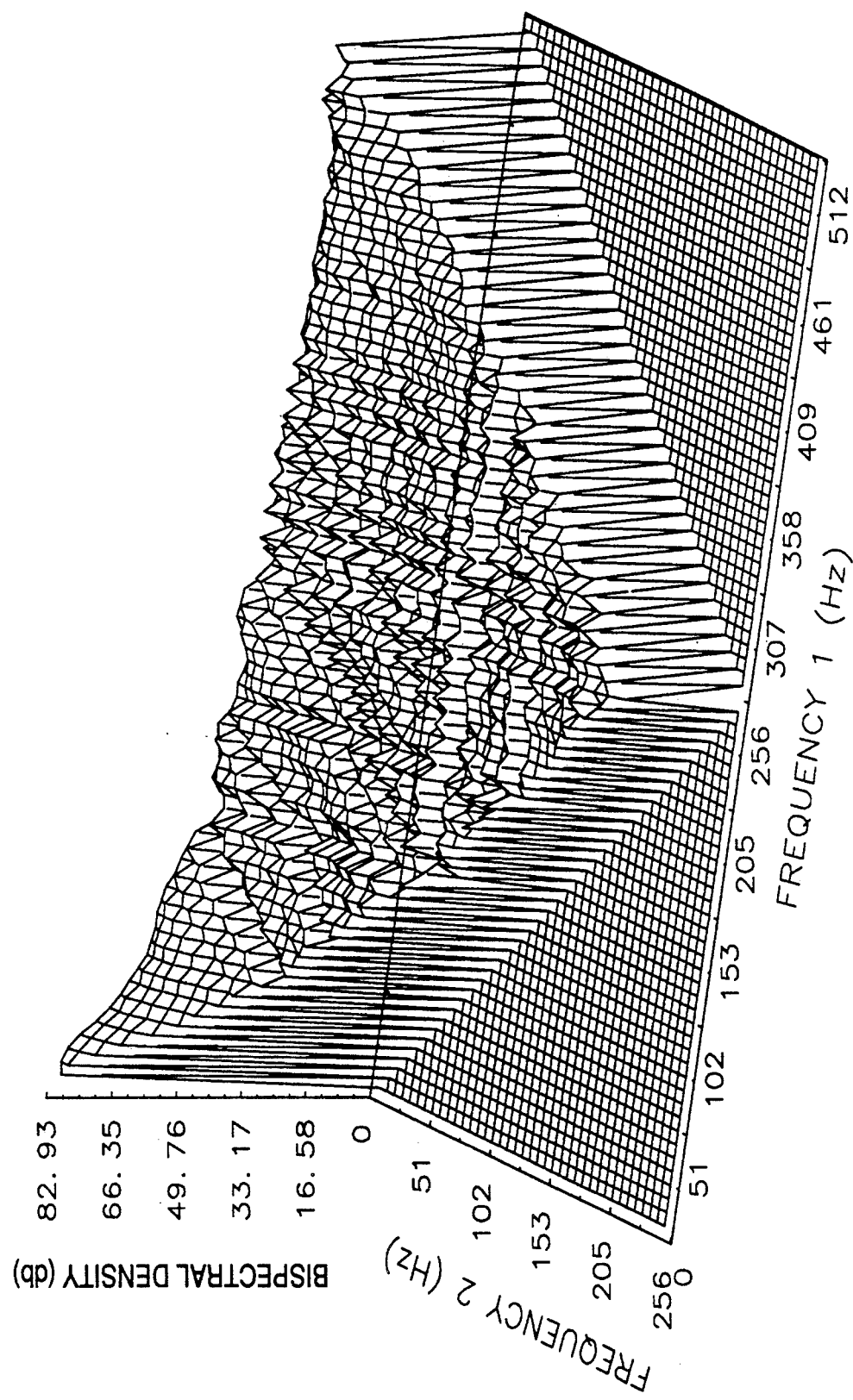
FIG. 11 are sample diagrams of autobispectral arrays of the QRS complex generated by the system and method of the present invention.
Figure 11B:
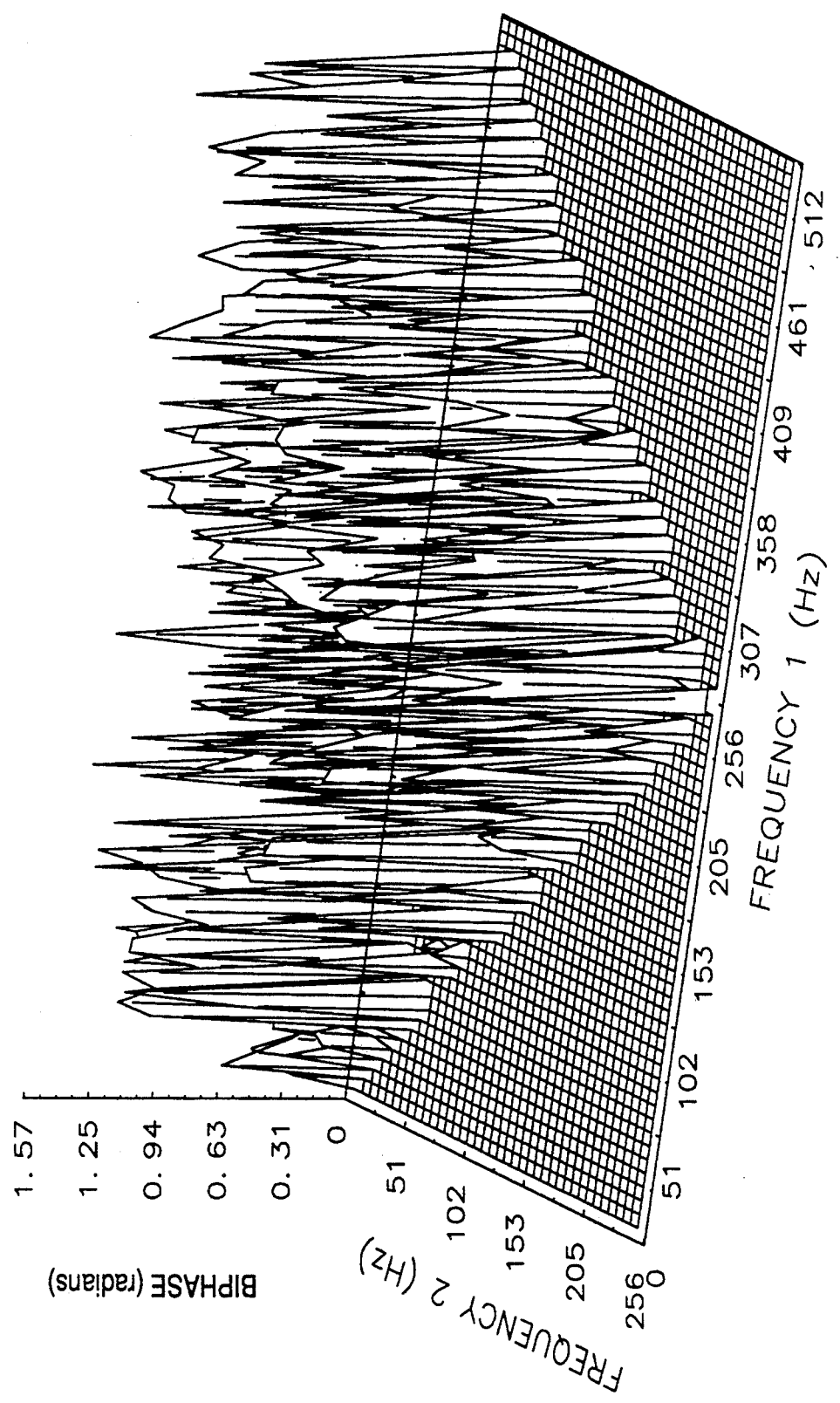
Figure 11C:
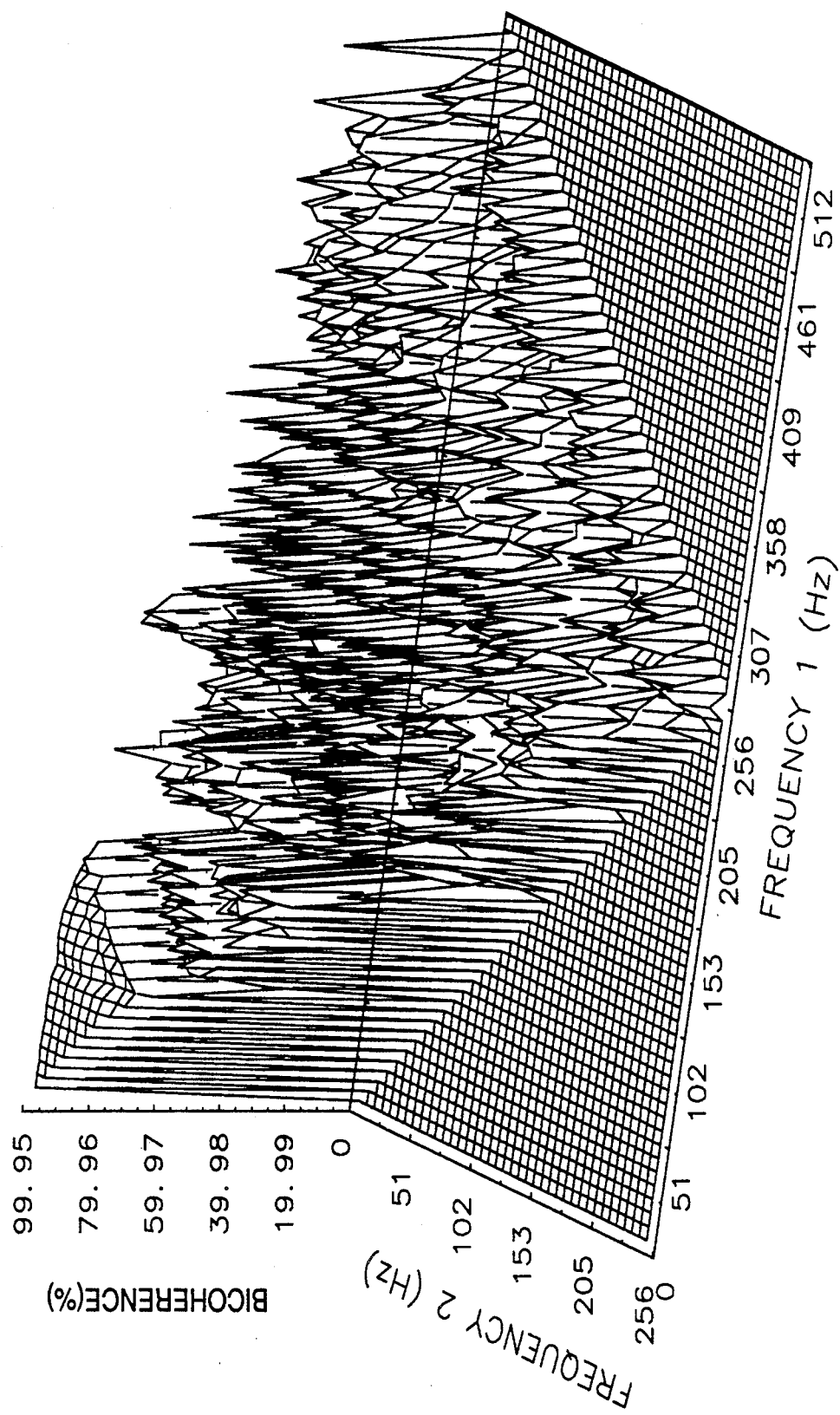

For illustration purposes FIG. 11 contains sample autobispectral arrays of the QRS complex showing frequency pairs $0 < f_1 < 512$ Hz, and $0 < f_2 < 256$ Hz. A bispectral density array is shown in FIG. 11(a) where the Z axis represents the magnitude in decibels (db) of the coupling interaction between all appropriate frequency pairs $f_1$ and $f_2$. Recall that the frequency pairing scheme must adhere to symmetry rule:

$$f_1 + f_2 < N/2$$

where N=1024 Hz in this case. A biphase array is shown in FIG. 11(b) where the Z axis represents the phase in radians of the coupling interaction between all appropriate frequency pairs $f_1$ and $f_2$. A bicoherence array is shown in FIG. 11(c) where the Z axis represents the normalized magnitude in percent (%) of the coupling interaction between all appropriate frequency pairs $f_1$ and $f_2$.

Figure 12:
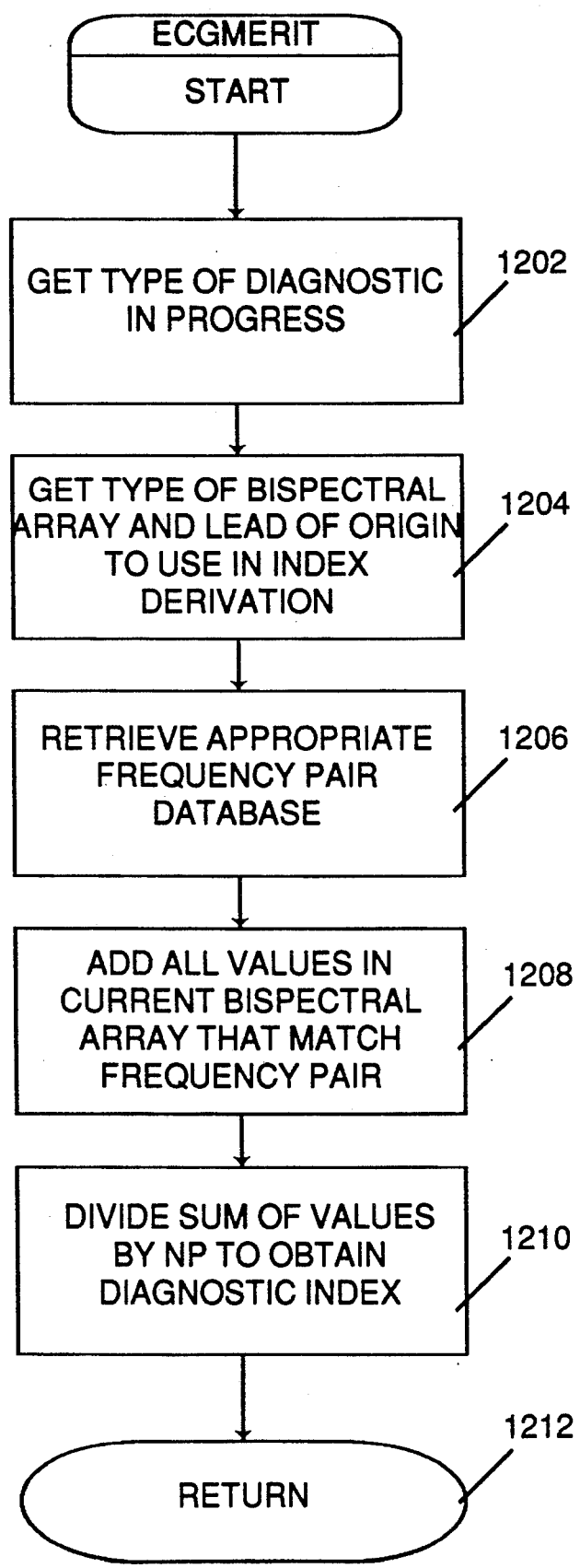
FIG. 12 is a flow chart of the steps used to generate diagnostic indices by the system and method of the present invention.

Referring now to FIG. 12 a more detailed outline of the diagnostic index generation module 410 is shown. In step 1202, the software identifies the type of diagnostic test in progress. The possible options include but are not limited to:

1. detection and quantification of coronary artery disease
2. detection and monitoring of myocardial ischemia
3. detection of reperfusion status post thrombolytic therapy
4. assessment of coronary artery restenosis after successful percutaneous transluminal coronary angioplasty
5. one-time or continuous monitoring of changes in cardiac electrical stability whether due to drugs, heart disease, acute infarction or neural factors.
6. one-time or continuous assessment of antiarrhythmic drug effects on cardiac electrical stability
7. assessment of the extent of malignancy of cardiac arrhythmias.
8. differentiation of sustained ventricular tachycardia from wide complex supraventricular tachycardia.
9. one time or continuous monitoring of neural inputs to the heart
10. evaluation of pump function and ejection fraction
11. identifying ongoing organ rejection in cardiac transplant patients.

In step 1204, the system retrieves the type of bispectral array to use in the diagnostic index computation as well the lead(s) of origin. We have 16 possible ECG leads and each lead could have 4 autobispectral arrays and 4 crossbispectral arrays for any portion of the complexes matching the template selected. These arrays do not include inter-lead crossbispectral arrays. The combination possibilities can lead to a very large number of computations associated with each diagnostic index as well as a substantial reference clinical database. Statistical methods to identify leads and bispectral arrays with the greatest diagnostic fidelity for each test are used to make this system practical. Such statistical methods will be discussed in greater detail below.

In step 1026, the appropriate reference array is retrieved from resident memory or from disk. Each reference array will contain the locations of the frequency pairs which are most sensitive to the diagnostic test in progress. In step 1208, all data points in the bispectral array at the locations identified by the retrieved reference array are added together for a single value index. A counter (NP) of the total number of points added is kept. In step 1210, the single value index is divided by NP to obtain the diagnostic index. In step 1212, the program returns to the monitor module 402.

The predetermined clinical reference arrays referred to above are critical to the device's ability to achieve clinically relevant diagnostic efficacy, and the process adopted for generating these clinical reference arrays will now be described. Since the total number of possible diagnostic applications will require many reference arrays, only two types of statistical approaches will be discussed in detail. All other reference arrays are acquired in a similar fashion utilizing a wide number of clinically appropriate statistical approaches. For illustration purposes the generation of the bicoherence reference array for detection of coronary artery disease with orthogonal lead X, assessment of risk to VT/VF with orthogonal lead Z, and assessment of ejection fraction with orthogonal lead X will be discussed in the following section.

In a first study raw ECG signals were acquired from two groups of subjects:

(a) young, medically healthy normal volunteers (n=28)
(b) older patients with normal conventional ECG's and angiography-proven coronary atherosclerosis (n=16)

The acquisition procedure described previously is followed:
Band pass filter 0.05–512 Hz
Sampling rate 1024 sample/sec
Number of bispectral averages performed k=100

FOr all subjects three minutes of artifact free ECG data were acquired. An autobicoherence array is generated from 100 QRS complexes from orthogonal lead X for all subjects. The arrays are grouped in 2 sets of arrays, the first representing the young normals and the second representing the coronary artery disease subjects.

A paired Student's t test is performed on each of 1640 data points, comparing the first and second sets of arrays. The resulting 1640 t values are stored in a two dimensional array identical in structure to that of the bicoherence array.

Each t value from t array (T(f1,f2)) is tested for significance based on the number of degrees of freedom. Where the degrees of freedom are equal to the total number of subjects—1. All t values not meeting the required significance level are set to 0. In the preferred embodiment all locations with a t value not corresponding to a $p<0.05$ are set to 0.

The application of the above conditions has the effect of identifying all of the frequency pair locations that are significantly different in coronary artery patients when compared to young normal volunteers. Suppression of all other frequency pairs allows easier inspection of the most sensitive regions.

Figure 13A:
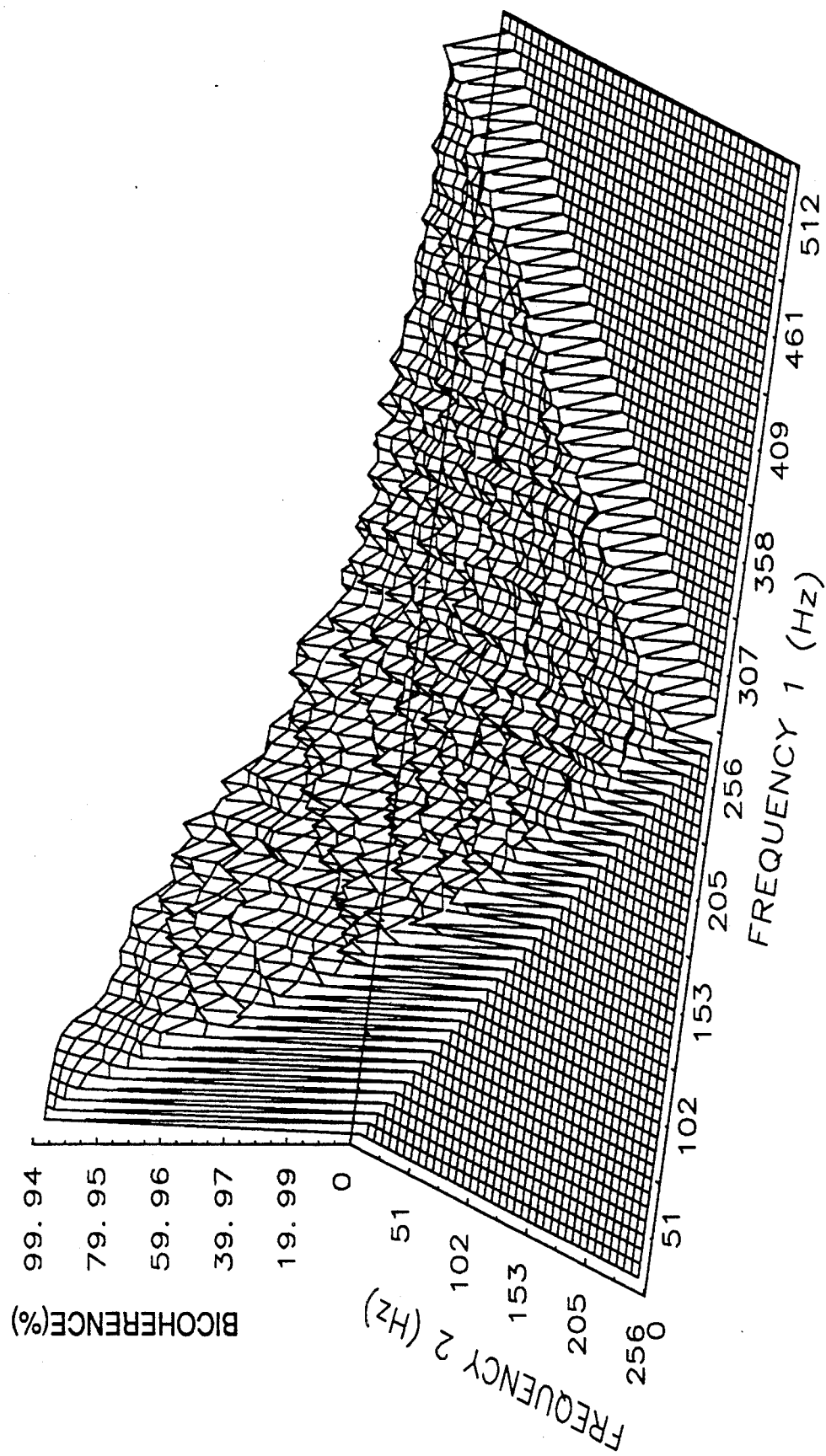
FIG. 13 are diagrams of several autobiocoherence arrays developed during the determination of the clinical reference arrays.
Figure 13B:
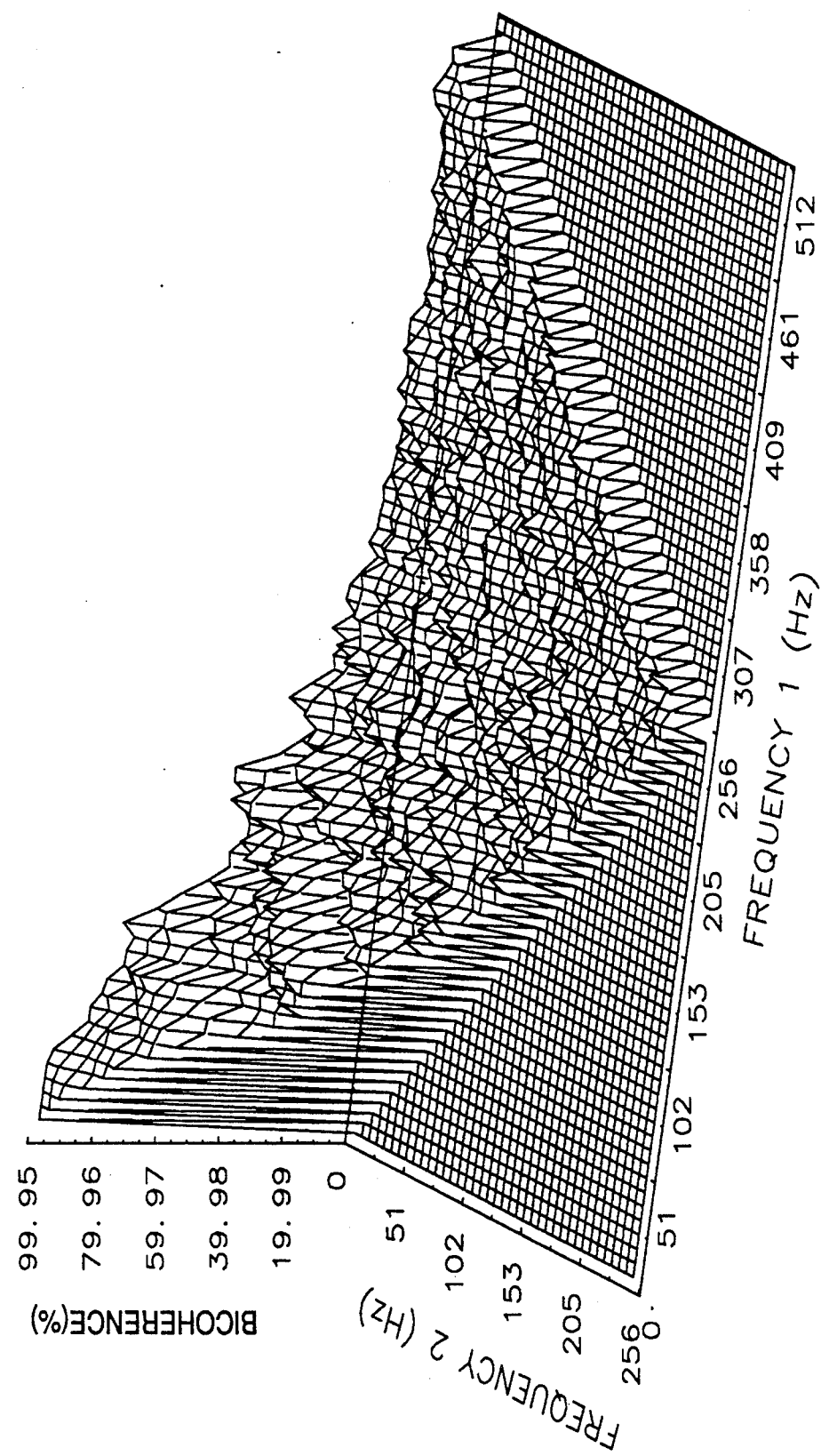
Figure 13C:
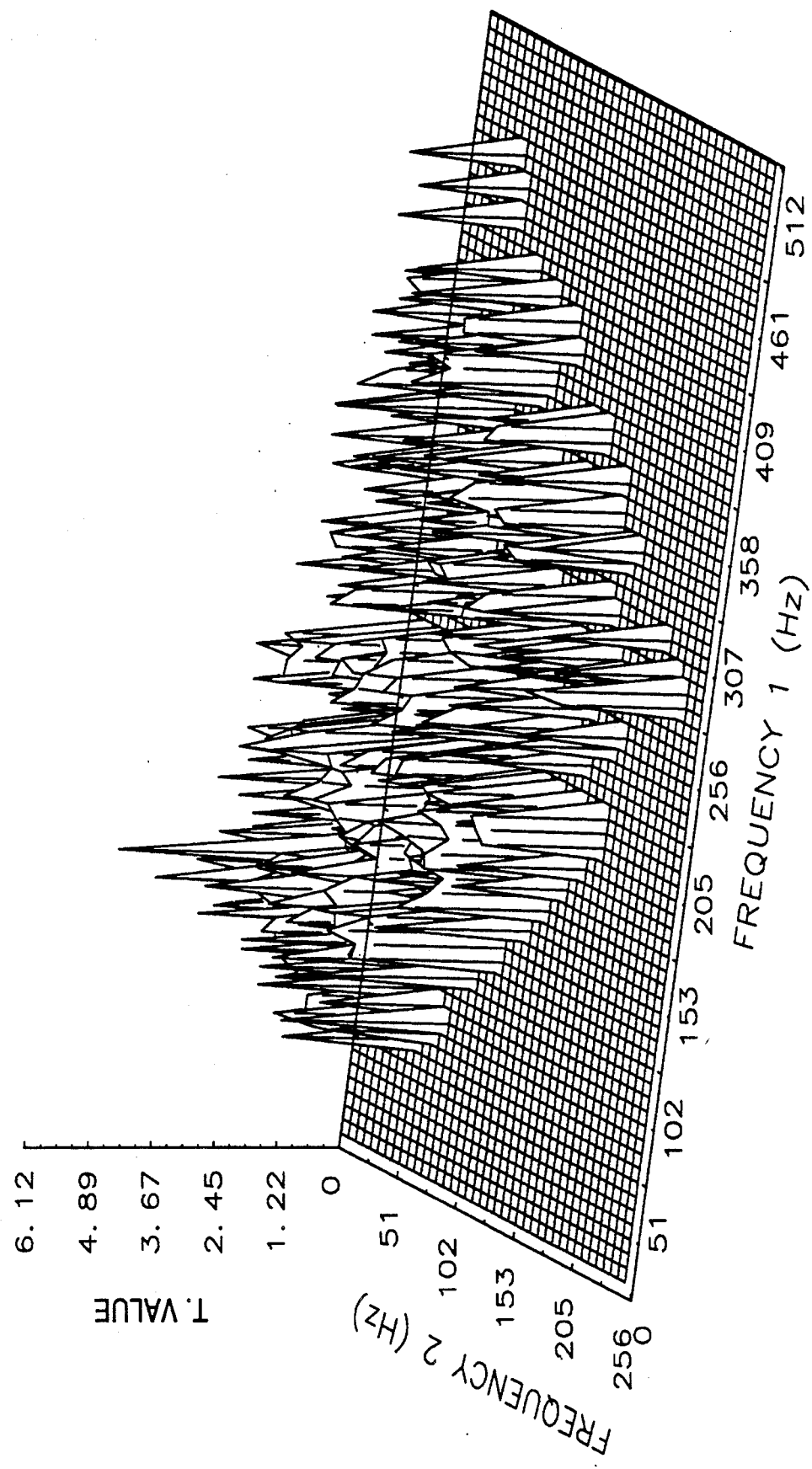

Turning now t FIG. 13, FIG. 13(a) shows the mean autobicoherence array for orthogonal lead X for the normal subjects. FIG. 13(b) shows the mean autobicoherence array for orthogonal lead Y for the CAD subjects. FIG. 13(c) shows the t array with all t values not meeting $P<0.05$ set to 0.

The next step involves sorting the t array for the most sensitive ensemble of frequency pair locations. In a preferred embodiment this would consist of the top 25% of all significant t values. The locations f1,f2 of the most significant t values will be used to generate a diagnostic index for each subject in the process described above. Table 14(a) of FIG. 14 shows sample indices for normal subjects and Table 14(b) shows sample indices for CAD subjects. The coded filename of the subject tested precedes each index.

The final step is to identify a cutoff value for the diagnostic index above which subjects are normal and al values below will indicate the presence of CAD. This cutoff should be optimized to yield the best sensitivity and specificity.

$$\text{Sensitivity} = \frac{\text{true positive tests}}{\text{all true positives}}$$

$$\text{Specificity} = \frac{\text{true negative tests}}{\text{all true negatives}}$$

In this particular case if we chose a cutoff of 20.0 the sensitivity and specificity will be 100%(16/16) and 96.4%(27/28) respectively.

The above statistical steps are repeated for all the possible bispectral arrays that can be generated (as described above) from all ECG leads acquired. To rank order the arrays with respect to diagnostic efficacy a second prospective study is conducted. The conditions under which the study is conducted are identical to those of the first except that: (a) the frequency pair locations of interest have already been identified and are now followed prospectively and (b) the size of the study group is now sufficient large so that sample variation of bispectral arrays more closely approximates the true variance within the population undergoing the intervention or suffering from the disease.

Thus for the example of coronary artery diagnosis, patients undergoing coronary angiography would each have a recording taken. The diagnostic index for each type of bispectral array from each lead or combination of leads would be calculated. These indices would then be compared to the results of angiography. The sensitivities and specificities for the detection of coronary disease would then be calculated for each bispectral array. The best array and lead system is then chosen as the default setting for the diagnostic procedure under consideration. The frequency locations identified by t values of this array will be used by the diagnostic index derivation module 410.

The above statistical approach may also be used to identify patients who are at risk of malignant arrhythmias. In a second study two new groups of patients are used:

(a) The control group consists of patients with previous anterior or inferior MI without a history of malignant ventricular arrhythmias (n=37).

(b) The arrhythmia group consists of patients with a history of previous anterior or inferior MI and a history of sustained ventricular tachycardia or out-of-hospital cardiac arrest (VT/VF) (n=12).

Figure 15A:
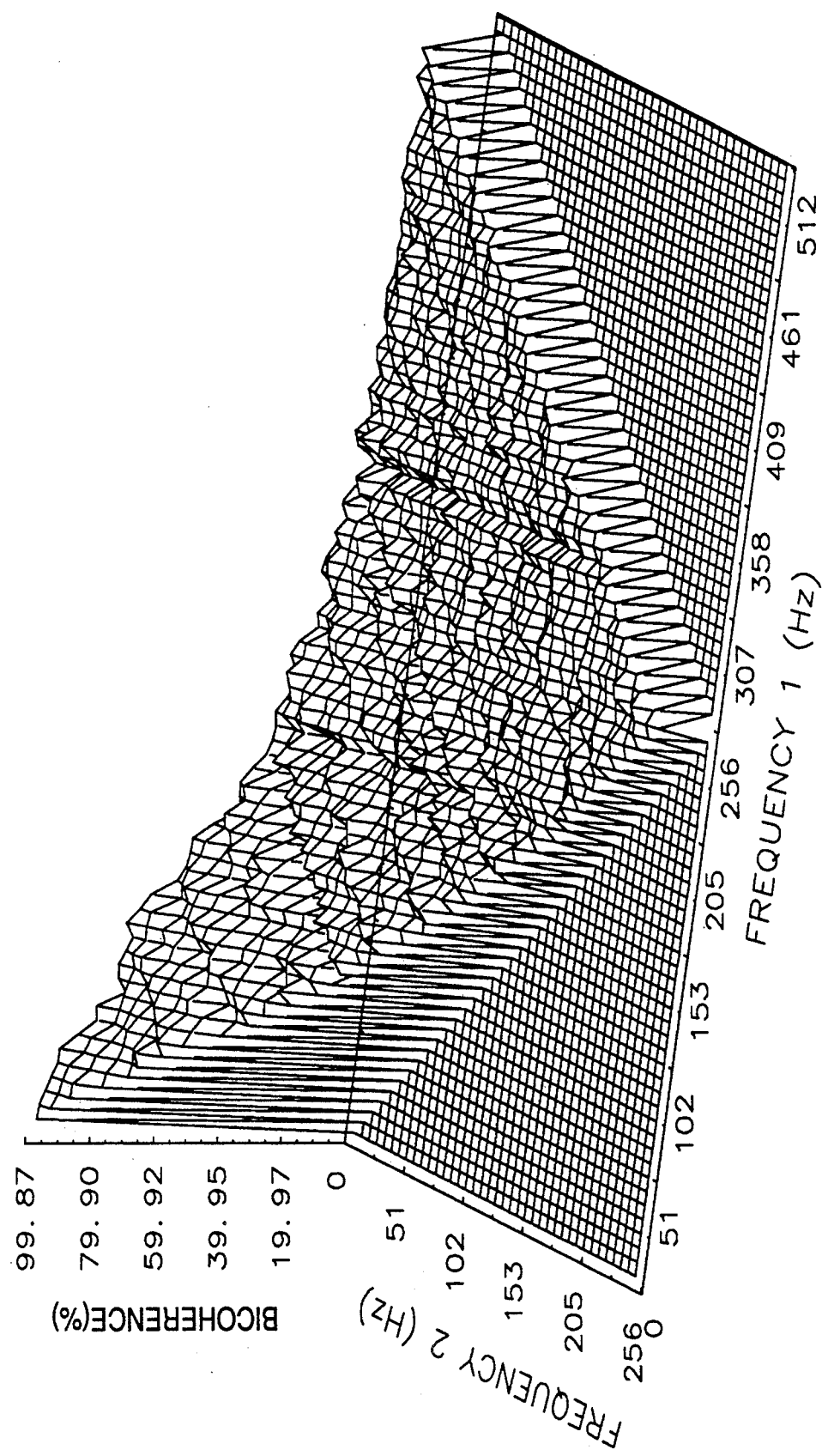
FIG. 15 are diagrams showing sample biocoherence values when the system and method of the present invention is used to identify patients at risk of malignant arrhythmias.
Figure 15B:
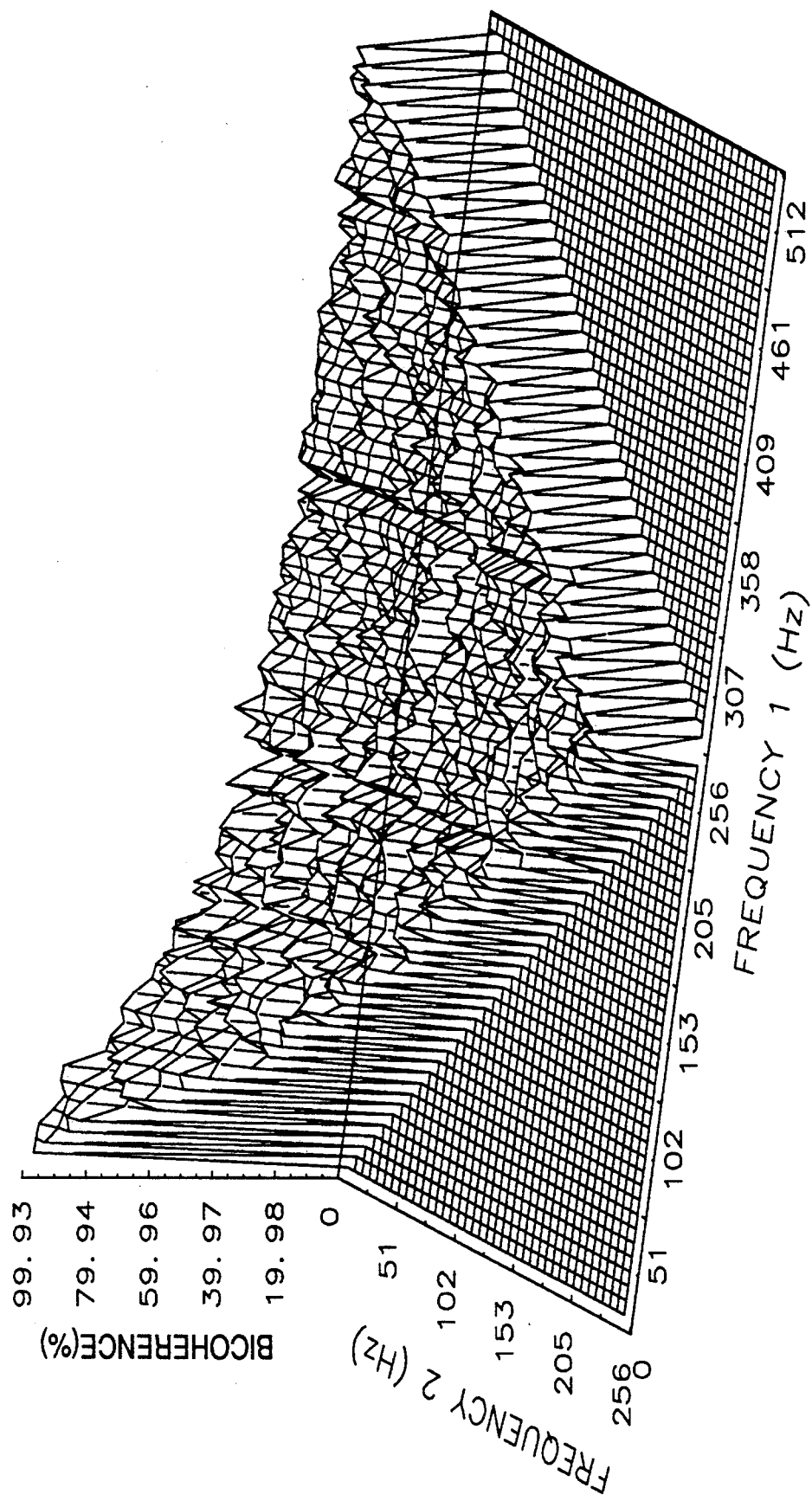
Figure 15C:
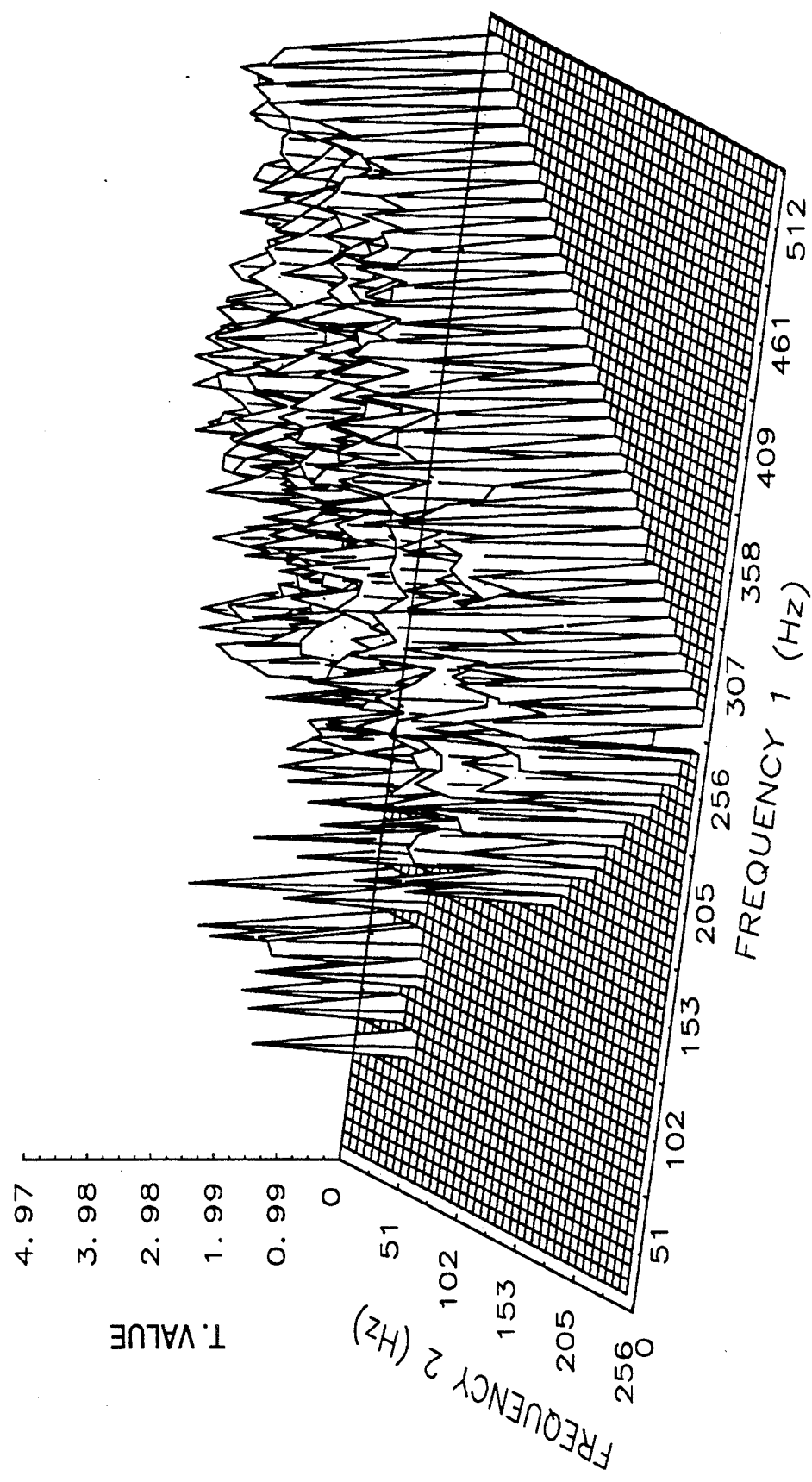

An autobicoherence array is generated from 100 QRS complexes from orthogonal lead Z for all subjects. The arrays are grouped in 2 sets of arrays, the first representing the MI subjects and the second representing the VT/VF subjects. After conducting the t test described earlier the statistical data shown in FIG. 15 was generated. FIG. 15(a) shows the mean autobicoherence array for orthogonal lead Z for the MI subjects. FIG. 15(b) shows the mean autobicoherence array for orthogonal lead Z for the VT/VF subjects. FIG. 15(c) shows the t array with all t values not meeting p<0.05 set to 0.

The t array generated is then used to produce diagnostic indices for both groups as shown earlier for the CAD study. The whole statistical process is followed through including prospective studies to identify the best bispectral array and its corresponding lead for the identification of patients who are at risk of malignant arrhythmias. Table 16(a) of FIG. 16 shows sample indices for MI subjects and Table 16(b) shows sample indices for the VT/VF subjects. The coded filename of the subject tested precedes each index. In this particular case if we chose a cutoff of 26.0, the sensitivity and specificity will be 91.6%(11/12) and 86.4%(32/37) respectively.

This invention is not limited to the use of the t test and many other statistical ranking test might be used when appropriate. For example if the diagnostic procedure requires the measurement of a continuous variable such as ejection fraction (EF) regression analysis is more suitably used.

Figure 17A:
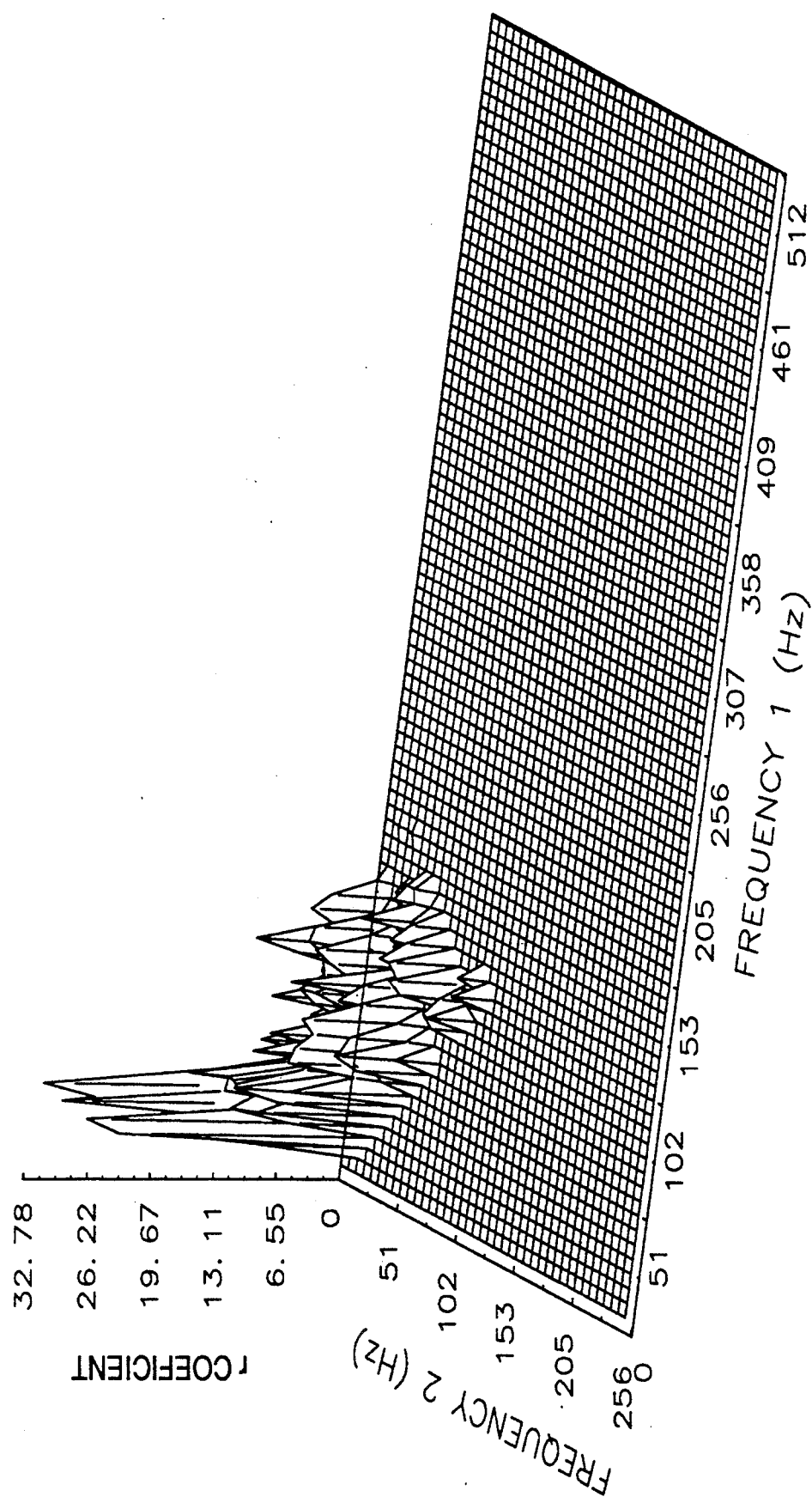
FIGS. 17(a)-17(b) are graphs of coefficients generated by the system and method of the present invention.
Figure 17B:
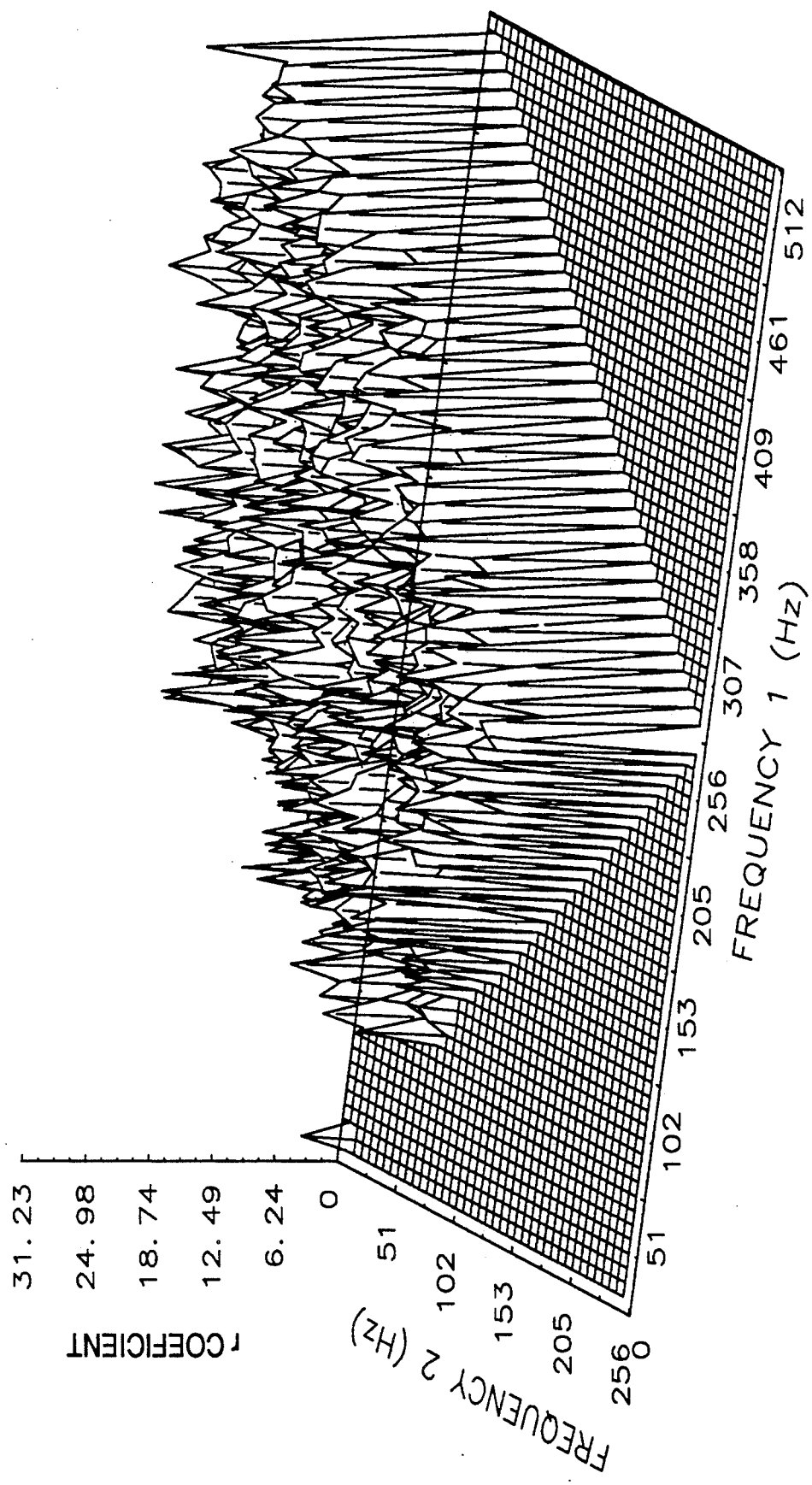

The following example will describe the use of the present invention to measure a continuous variable. In this example, raw ECG signals were acquired from a large number of patients (n=247) with known EF through ventriculography. The autobicoherence array from 100 QRS complexes for lead X was computed. Each one of the 1640 bicoherence points was correlated with its corresponding EF value across all patients. The outcome is a two dimensional array similar in structure to that of the bicoherence array and where the value at each (f1,f2) represents the r regression coefficient between the bicoherence at this frequency pair and ejection fraction. The r coefficient will range from −1 to 1. The results are shown in FIG. 17. FIG. 17(a) shows the positive r values between EF and bicoherence at the corresponding frequency pairs, and FIG. 17(b) shows the negative r values.

In addition to quantifying the presence and extent of coronary artery disease (CAD), myocardial ischemia, cardiac electrical stability, risk of malignant ventricular arrhythmia, site(s) of origin of malignant arrhythmias, extent of malignancy of arrhythmias, degree of antiarrhythmic drug efficacy, neural and humoral inputs to the heart, pump function/ejection fraction, and ongoing organ rejection in cardiac transplant patients, the system and method of the present invention may also be used to assess a myriad of cardiac phenomena based on the acquisition and processing of ECG signals into various bispectral arrays which are then compared to appropriate reference arrays.

Although power spectral analytic techniques in the frequency domain have been applied to the ECG signal, as was discussed in the Background above, higher order spectra whether by FFT or by parametric approaches having never been so applied. No bispectral technique has ever been demonstrated to be useful for any diagnostic purpose. Other techniques for the quantification of coronary artery disease, PTCA restenosis or the detection of cardiac electrical instability, especially as it changes with antiarrhythmic drug administration, remain qualitative, static and limited in their overall utility and acceptance in practice. Specifically, the system and method of the present invention uses various bispectral values to measure dynamic frequency structure [higher order phase-locking] across all frequency pairs in a frequency range ignored by those knowledgeable in the art and uses various alterations in these bispectral parameters at a limited number of frequency locations as an index of physiological perturbation. The system an method utilizes various bispectral arrays of transformed ECG signals of defined clinical populations to define the locations of the subset of frequencies used to calculate this index. Reference clinical arrays are further utilized to assess the meaning of this index and to measure the significance of deviations of this index from normality. This allows the quantitative gauging of the disturbances in cardiac function, whether due to coronary disease, electrical instability, restenosis after PTCA, drugs or ischemia for any particular ECG lead position. The invention disclosed here also defines the graphic display of the diagnostic index, whether on video screen or on paper, whether in real-time or in digital archive.

While the foregoing invention has been described with reference to its preferred embodiments, various alterations and modifications will occur to those skilled in the art. For example, the ECG may carry diagnostic information at frequencies much higher than the cutoff frequency of 512 Hz. The use of such high frequency low energy components of the ECG waveform by the system and method described above is intended to fall within the scope of the current invention. All such alterations and modifications are intended to fall within the scope of the appended claims.

What is claimed is:

1. A method of noninvasively detecting cardiac phenomena comprising the steps of:
   acquiring electrocardiographic signals from a body surface of a subject being analyzed through a surface electrode;
   determining a waveform template representing a QRST waveform in said subject;
   selecting a number of signals that match said waveform template and storing said signals for processing;
   generating bispectral values from selected signals, comparing said bispectral values to reference bispectral values to analyze cardiac phenomena.

2. The method of noninvasively detecting cardiac phenomena of claim 1 wherein said generated bispectral values are autobispectral density values.

3. The method of noninvasively detecting cardiac phenomena of claim 1 wherein said generated bispectral values are autobicoherence values.

4. The method of noninvasively detecting cardiac phenomena of claim 1 wherein said generated bispectral values are autobiphase values.

5. The method of noninvasively detecting cardiac phenomena of claim 1 wherein said step of selecting a number of signals that match said waveform template comprises the step of selecting pairs of successive time series records that are used in the generation of bispectral values.

6. The method of noninvasively detecting cardiac phenomena of claim 5 wherein said generated bispectral values are crossbispectral density values.

7. The method of noninvasively detecting cardiac phenomena of claim 5 wherein said generated bispectral values are crossbispectral density values.

8. The method of noninvasively detecting cardiac phenomena of claim 5 wherein said generated bispectral values are crossbiphase values.

9. The method of noninvasively detecting cardiac phenomena of claim 1 further comprising the step of comparing said bispectral values to reference bispectral values to detect a presence and extent of coronary artery disease in said subject.

10. The method of noninvasively detecting cardiac phenomena of claim 1 further comprising the step of comparing said bispectral values to reference bispectral values to detect a presence and extent of myocardial ischemia in said subject.

11. The method of noninvasively detecting cardiac phenomena of claim 1 further comprising the step of comparing said bispectral values to reference bispectral values to analyze cardiac electrical stability in said subject.

12. The method of noninvasively detecting cardiac phenomena of claim 1 further comprising the step of comparing said bispectral values to reference bispectral values to analyze a risk of malignant ventricular arrhythmia in said subject.

13. The method of noninvasively detecting cardiac phenomena of claim 1 further comprising the step of comparing said bispectral values to reference bispectral values to locate a site of origin of malignant arrhythmias in said subject.

14. The method of noninvasively detecting cardiac phenomena of claim 1 further comprising the step of comparing said bispectral values to reference bispectral values to analyze an extent of malignancy of arrhythmias in said subject.

15. The method of noninvasively detecting cardiac phenomena of claim 1 further comprising the step of comparing said bispectral values to reference bispectral values to evaluate a degree of antiarrhythmic drug efficacy in said subject.

16. The method of noninvasively detecting cardiac phenomena of claim 1 further comprising the step of comparing said bispectral values to reference bispectral values to examine neutral and humoral inputs to the heart of said subject.

17. The method of noninvasively detecting cardiac phenomena of claim 1 further comprising the step of comparing said bispectral values to reference bispectral values to evaluate pump function or ejection fraction in the heart of said subject.

18. The method of noninvasively detecting cardiac phenomena of claim 1 further comprising the step of comparing said bispectral values to reference bispectral values to monitor ongoing organ rejection wherein said subject is a cardiac transplant patient.

19. The method of noninvasively detecting cardiac phenomena of claim 1 further comprising the step of distinguishing wide-complex supraventricular tachycardia from sustained ventricular tachycardia.

20. The method of noninvasively detecting cardiac phenomena of claim 1 wherein said step of generating bispectral values comprises:
   assigning each selected signal matching said waveform template to a time series record;
   computing an average complex triple product using Fourier transforms of said time series records;
   computing biphase values as the inverse tangent of the quotient of an imaginary part of the average complex triple product divided by a real part of the average complex triple product.

21. The method of noninvasively detecting cardiac phenomena of claim 20 wherein said biphase values are crossbiphase values.

22. The method of noninvasively detecting cardiac phenomena of claim 20 wherein said biphase values are autobiphase values.

23. The method of noninvasively detecting cardiac phenomena of claim 1 wherein said step of generating bispectral values comprises:
   assigning each selected signal matching said waveform template to a time series record;
   determining Fourier transforms of said time series records;
   estimating bispectrum of said time records by computing sequences of third-order moments, forming super matrices using said third-order moments, determining orders of autoregressive model filters of the bispectrum of the Fourier transforms of said time records from ranks of said super matrices, obtaining the skewness and autoregressive filter coefficients by; solving a set of equations based on said third order moments and said order, and computing said bispectrum from said skewness and autoregressive filter coefficients.

24. The method of noninvasively detecting cardiac phenomena of claim 23 further comprising the step of estimating power spectra of said Fourier transforms, said step of estimating power spectra comprising the steps of:
   computing two sequences of autocorrelations and performing a recursion function on each autocorrelation sequence in order to determine final prediction errors, minimums of said final prediction errors being order of the autoregression filters of said power spectra;
   performing a recursion function on said autocorrelation sequences using said order of the autoregression filters in order to generate coefficient of said autoregression filters;
   computing the power spectra as the final prediction error divided by a square of the magnitude of the Fourier transform of said coefficients.

25. The method of noninvasively detecting cardiac phenomena of claim 24 further comprising the steps of:
   computing a real triple product as the product of three power spectra values;
   computing an array of bicoherence values as the quotient of bispectral density divided by a square root of said real triple product.

26. The method of noninvasively detecting cardiac phenomena of claim 23 wherein said step of computing bispectrum of said Fourier transforms of said time series records comprises dividing the cubic root of the product of three skewnesses by a triple product of the Fourier transforms of the AR filter coefficient.

27. The method of noninvasively detecting cardiac phenomena of claim 23 further comprising the step of computing an array of bispectral densities by determining the absolute value for each bispectrum value.

28. The method of noninvasively detecting cardiac phenomena of claim 23 further comprising the step of computing an array of biphase values as the inverse tangent of the quotient of an imaginary part of the bispectrum divided by a real part of the bispectrum.

29. The method of noninvasively detecting cardiac phenomena of claim 1 wherein said bispectral values are crossbispectral values generated from consecutive signals from one surface electrode.

30. The method of noninvasively detecting cardiac phenomena of claim 1 wherein said bispectral values are crossbispectral values generated from signals obtained from two surface electrodes.

31. The method of noninvasively detecting cardiac phenomena of claim 1 wherein said template is a sinus rhythm template.

32. The method of noninvasively detecting cardiac phenomena of claim 1 wherein said template is an ectopic beat template.

33. The method of noninvasively detecting cardiac phenomena of claim 1 further comprising the steps of generating clinical reference arrays for use in identifying particular bispectral values that are sensitive to the cardiac phenomena being analyzed.

34. The method of noninvasively detecting cardiac phenomena of claim 33 further comprising the step of rank ordering said clinical reference arrays with respect to the diagnostic efficacy of the arrays for the cardiac phenomena being analyzed.

35. The method of noninvasively detecting cardiac phenomena of claim 33 wherein values in said clinical reference arrays that are not significant are suppressed to facilitate inspection of the most sensitive values.

36. The method of noninvasively detecting cardiac phenomena of claim 33 further comprising the steps of determining a diagnostic index from said clinical reference array, generated values above said index indicating a normal condition and below said index indicating an abnormal condition.

37. The method of noninvasively detecting cardiac phenomena of claim 36 wherein said diagnostic index is optimized to yield the best sensitivity and specificity with sensitivity being equal to true positives divided by positives and specificity being equal to true negatives divided by negatives.

38. The method of noninvasively detecting cardiac phenomena of claim 1 wherein said bispectral values are generated by computing the Fourier transform of the third order autocorrelation function of said filtering signals.

39. The method of noninvasively detecting cardiac phenomena of claim 1 wherein said bispectral values are generated by computing the Fourier transform of the third order crosscorrelation function of said filtered signals.

40. A system noninvasively detecting cardiac phenomena comprising:
   means for acquiring electrocardiographics signals from a surface of a body of a subject being analyzed;
   means for determining a waveform template representing a normal QRST waveform in said subject;
   means for selecting a number of signals that match said waveform template;
   means for storing said selected signals for processing;
   means for generating bispectral values from said selected signals and for comparing said bispectral values to reference bispectral values to detect and analyze cardiac phenomena.

41. The system for noninvasively detecting cardiac phenomena of claim 40 wherein said bispectral values are crossbiphase values.

42. The system for noninvasively detecting cardiac phenomena of claim 40 wherein said bispectral values are autobiphase values.

43. The system for noninvasively detecting cardiac phenomena of claim 40 wherein said bispectral values are autobispectral density values.

44. The system for noninvasively detecting cardiac phenomena of claim 40 wherein said bispectral values are crossbispectral density values.

45. The system for noninvasively detecting cardiac phenomena of claim 40 wherein said bispectral values are autobicoherence values.

46. The system for noninvasively detecting cardiac phenomena of claim 40 wherein said bispectral values are crossbicoherence values.

47. The system for noninvasively detecting cardiac phenomena of claim 40 wherein said means for acquiring electrocardiographic signals is a plurality of surface electrodes and wherein said bispectral values are crossbispectral values generated from consecutive signals from at least one of said plurality of said surface electrodes.

48. The system for noninvasively detecting cardiac phenomena of claim 40 wherein said means for acquiring electrocardiographic signals is a plurality of surface electrodes and wherein said bispectral values are cross-bispectral values generated from signals obtained from two of said surface electrodes.

49. The system for noninvasively detecting cardiac phenomena of claim 40 wherein said template is an ectopic beat template.

50. The system for noninvasively detecting cardiac phenomena of claim 41 further comprising means for generating clinical reference arrays for use in identifying particular bispectral values that are sensitive to the cardiac phenomena being detected and analyzed.

51. The system for noninvasively detecting cardiac phenomena of claim 41 further comprising means for automatically rank ordering clinical reference arrays of said reference bispectral values with respect to diagnostic efficacy of the arrays for the cardiac phenomena being detected and analyzed.

52. The system for noninvasively detecting cardiac phenomena of claim 41 further comprising means for suppressing values in clinical reference arrays of said reference bispectral values that are not significant in order to facilitate inspection of values most likely to indicate the presence of the cardiac phenomena.

53. The system for noninvasively detecting cardiac phenomena of claim 41 further comprising means for determining a diagnostic index from clinical reference arrays of said reference bispectral values, generated values above said index indicating a normal condition and values below said index indicating an abnormal condition.

54. The system for noninvasively detecting cardiac phenomena of claim 53 wherein said diagnostic index is optimized to yield the best sensitivity and specificity with sensitivity being equal to true positive tests divided by all true positives and specificity being equal to true negative tests divided by all true negatives.

55. The system for noninvasively detecting cardiac phenomena of claim 41 wherein said means for generating bispectral values comprises a means for computing the Fourier transform of the third order autocorrelation function of said filtered signals.

56. The system for noninvasively detecting cardiac phenomena of claim 41 wherein said means for generating bispectral values comprises a means for computing the Fourier transform of the third order crosscorrelation function of said filtered signals.

* * * * *